United States Patent
Erez et al.

[11] Patent Number: 5,921,963
[45] Date of Patent: *Jul. 13, 1999

[54] SKIN PIERCING DEVICES FOR MEDICAL USE

[75] Inventors: Uri Erez, Kiryat Motzkin; Yuval Singer, Haifa, both of Israel

[73] Assignee: Mali-Tech Ltd., Haifa, Israel

[*] Notice: This patent is subject to a terminal disclaimer.

[21] Appl. No.: 08/697,293

[22] Filed: Aug. 26, 1996

Related U.S. Application Data

[63] Continuation of application No. 08/325,412, Dec. 30, 1994, Pat. No. 5,578,014, and application No. PCT/US93/03992, Apr. 28, 1993.

[30] Foreign Application Priority Data

Apr. 29, 1992 [IL] Israel ......................................... 101720
Jan. 8, 1993 [IL] Israel ......................................... 104350

[51] Int. Cl.⁶ .................................................. A61M 5/00
[52] U.S. Cl. ............................................................ 604/192
[58] Field of Search .................................. 604/113, 110, 604/117, 187, 192, 198, 218, 263; 128/919; 606/167, 170, 172, 181, 182

[56] References Cited

U.S. PATENT DOCUMENTS

| | | | |
|---|---|---|---|
| 2,536,001 | 6/1950 | Chase | 62/91.5 |
| 2,674,246 | 4/1954 | Bower | 604/198 |
| 3,134,380 | 5/1964 | Armao | 604/198 |
| 3,605,742 | 9/1971 | Tibbs | 128/218 |
| 4,270,537 | 6/1981 | Romaine | 128/218 |
| 4,373,526 | 2/1983 | Kling | 128/215 |
| 4,564,054 | 1/1986 | Gustavsson | 604/198 |
| 4,600,281 | 7/1986 | Bloomstein . | |
| 4,613,328 | 9/1986 | Boyd | 604/156 |
| 4,646,737 | 3/1987 | Seney | 128/303.1 |
| 4,725,265 | 2/1988 | Sairenji | 604/112 |
| 4,775,369 | 10/1988 | Schwartz | 604/263 |
| 4,795,432 | 1/1989 | Karczmer | 604/198 |
| 4,801,295 | 1/1989 | Spencer | 604/198 |
| 4,863,436 | 9/1989 | Glick | 604/198 |
| 4,919,134 | 4/1990 | Streeter | 128/400 |
| 4,930,956 | 6/1990 | Mantovani . | |
| 5,066,288 | 11/1991 | Deniega | 604/274 |
| 5,130,815 | 7/1992 | Silverman et al. . | |
| 5,147,375 | 9/1992 | Sullivan | 606/182 |
| 5,318,547 | 6/1994 | Altschuler | 604/198 |
| 5,339,166 | 8/1994 | LeBrat et al. . | |
| 5,578,014 | 11/1996 | Erez et al. | 604/192 |

FOREIGN PATENT DOCUMENTS

| | | |
|---|---|---|
| 378042 | 7/1990 | European Pat. Off. . |
| 540403 | 5/1993 | European Pat. Off. . |
| 3325046 | 1/1985 | Germany . |
| 3320364 | 2/1985 | Germany . |
| 677633 A5 | 6/1991 | Switzerland . |
| 2101795 | 1/1983 | United Kingdom . |

OTHER PUBLICATIONS

Call It Amazing, by Jum St. Lawrence in "Videography".
Brochure from Dubner International, re Scene Stealer.
Sony brochure re BVE–9100.
Brochure from EVE, Espace Video Film in French and English.
pp. 3–8 and Fig. 1 from handbook from TDF–CERIM–laboratoire Audiofrequence.
Pamphlet entitled Project Aries Cahier Des Charges from Societe Aries.
BYTE, vol. 18, No. 2, Feb. 1993, pp. 225–228 and 230, Davis, et al, The Mac Goes to the Movies.
Proceedings of the International Conference On Data Engineering, Vienna, Apr. 19–23, 1993, No. Conf. 9, IEEE, pp. 381–390, Gibbs, et al., Audio/Video Databases: An Object–t–Oriented Approach.

*Primary Examiner*—John D. Yasko
*Assistant Examiner*—Manuel Mendez
*Attorney, Agent, or Firm*—Ladas & Parry

[57] ABSTRACT

Apparatus for piercing skin including a skin contact surface arranged to contact a portion of skin to be pierced, a skin piercing needle arranged to pierced the skin within the region and a cooling assembly providing cooling of the skin contact surface thereby cooling the portion of skin prior to and during piercing thereof by the skin piercing needle.

10 Claims, 19 Drawing Sheets

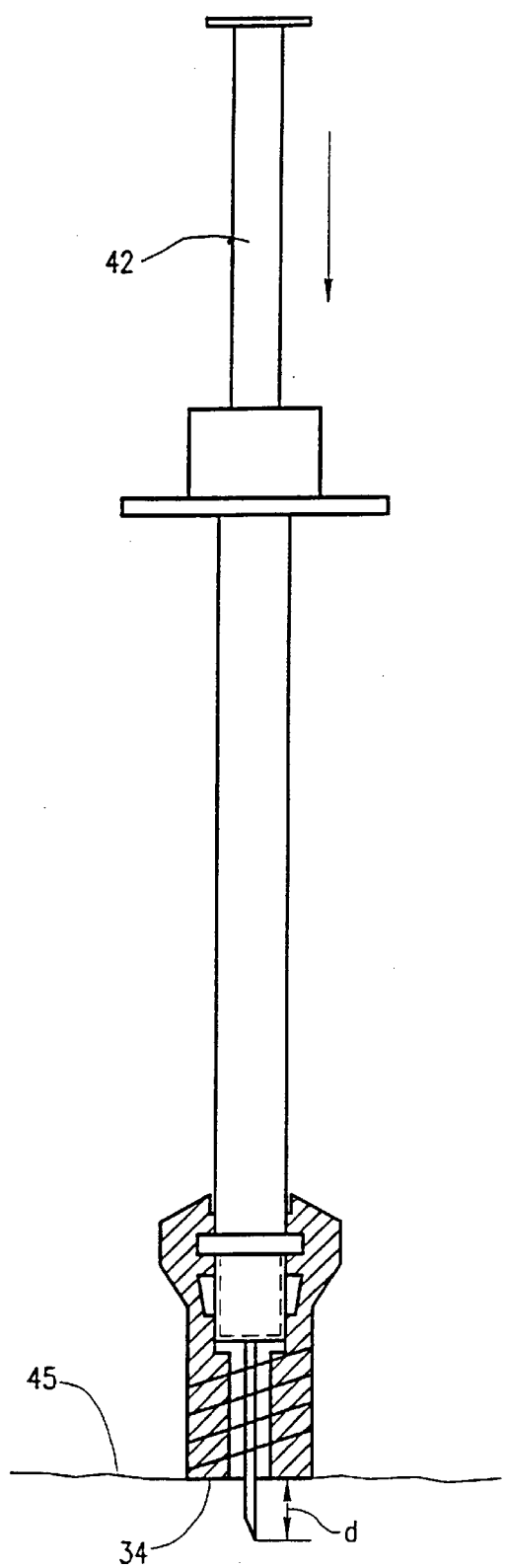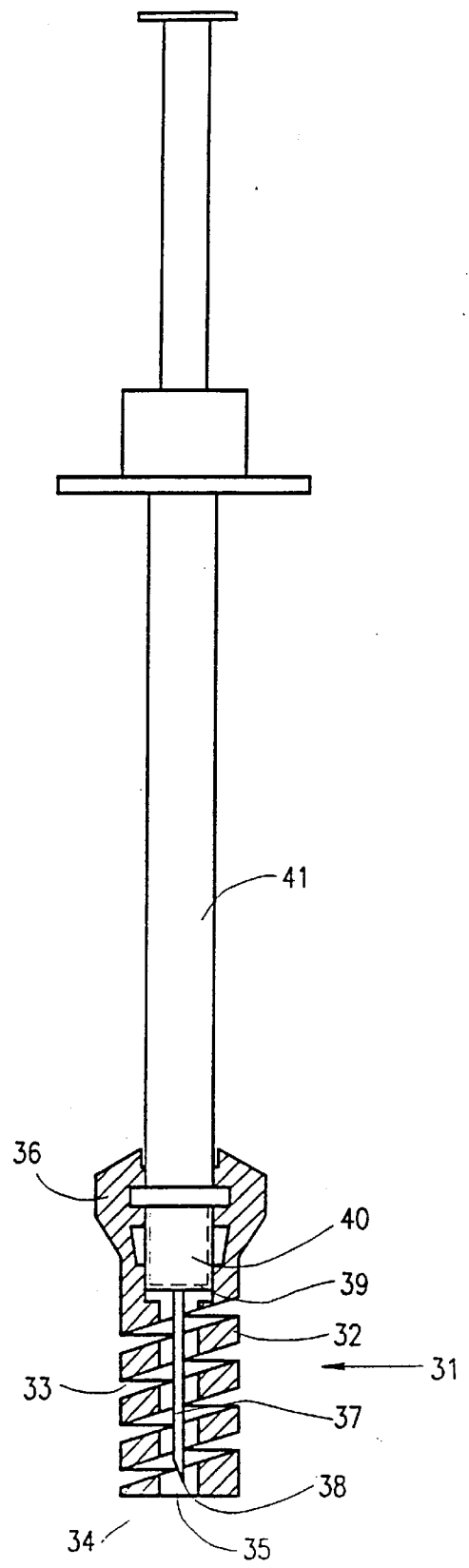
FIG.4B
FIG.4A

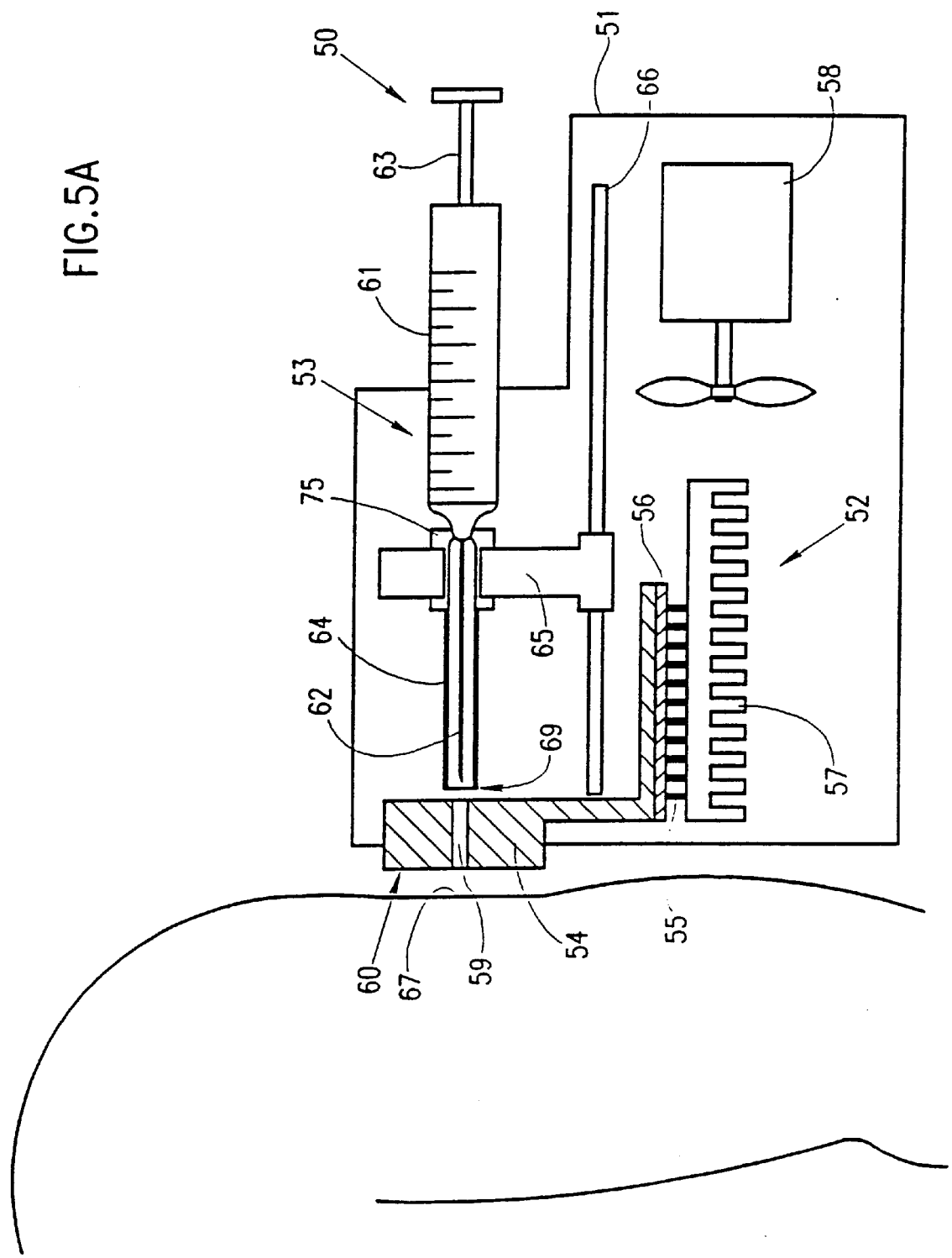

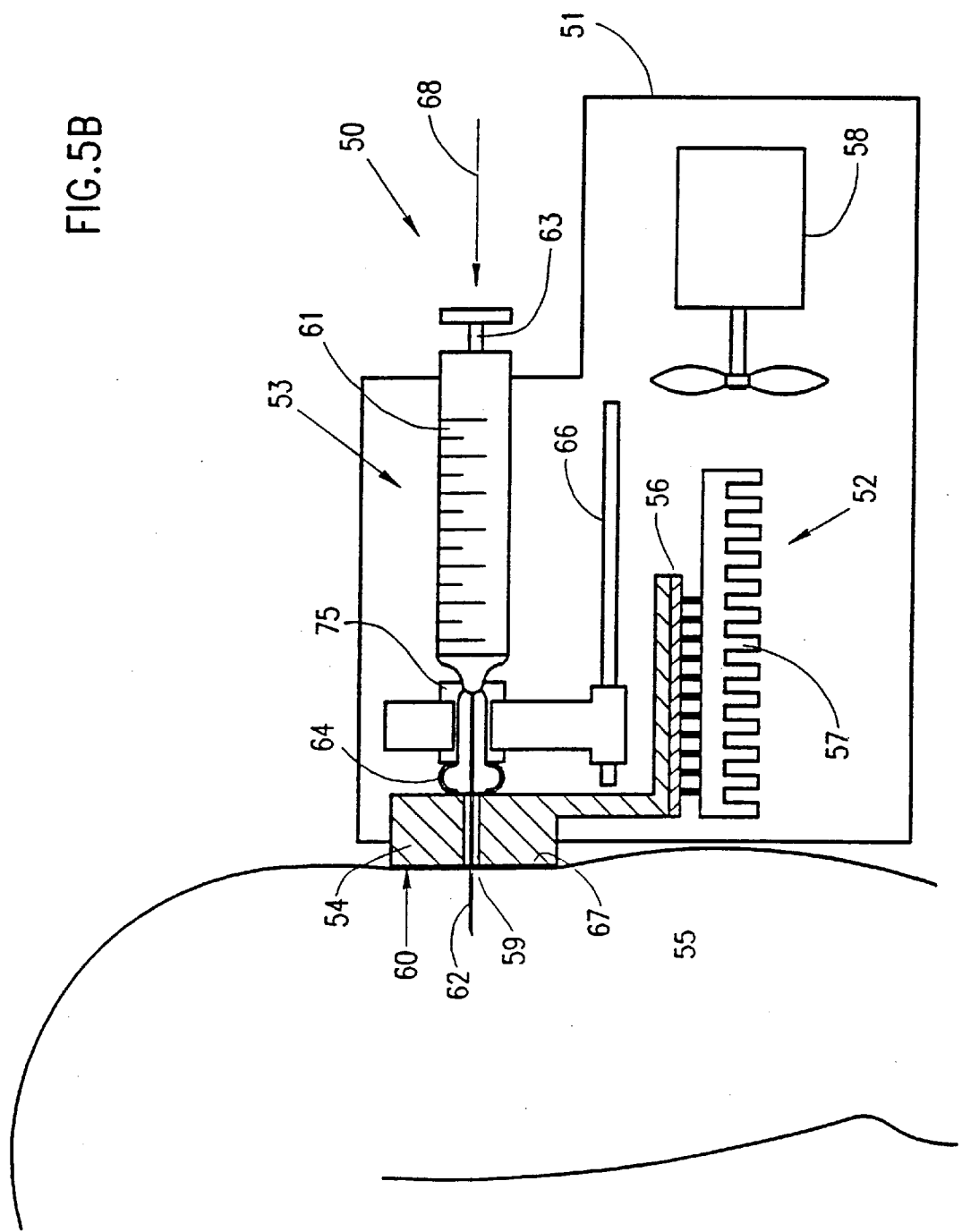

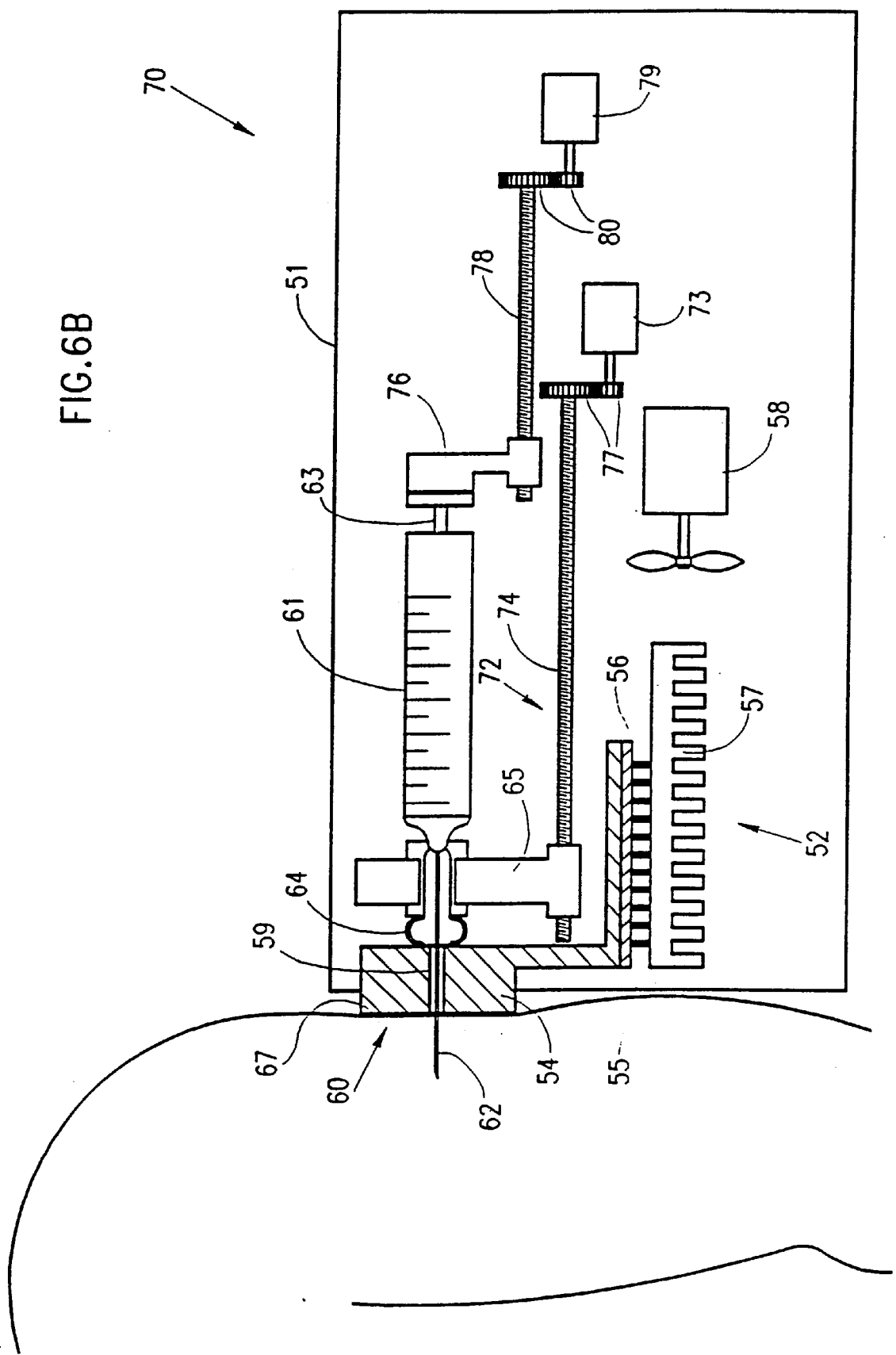

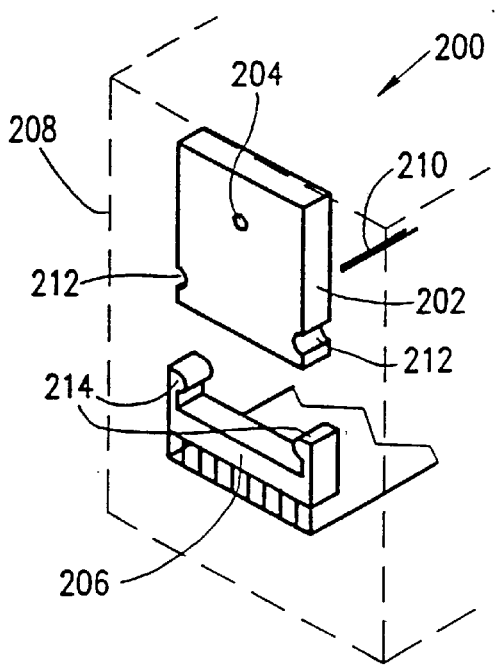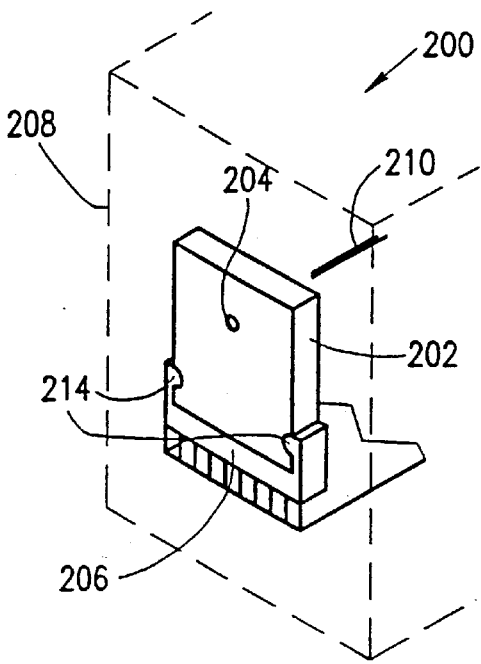
FIG.17A  FIG.17B
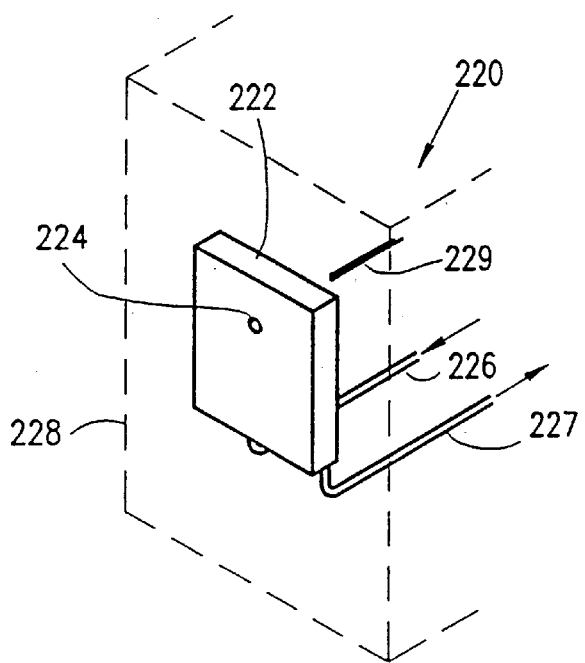
FIG.18

SKIN PIERCING DEVICES FOR MEDICAL USE

This is a continuation of application Ser. No. 08/325,412 filed on Dec. 30, 1994, now U.S. Pat. No. 5,578,014 and International Application PCT/US93/03992 filed on Apr. 28, 1993 and which designated the U.S.

FIELD OF THE INVENTION

The present invention relates to skin-piercing devices for medical use, and to cooling devices.

BACKGROUND OF THE INVENTION

The piercing of skin for purposes of administering medications and taking blood samples is well known in medical practice. Insertion of a needle into the skin is known to be accompanied by a localized sensation of pain. Accordingly, it would be an advantage to desensitize skin into which a needle is being introduced.

Various devices and methods are known in the prior art for local desensitization of skin. Among prior art publications which describe localized desensitization of skin are U.S. Pat. Nos. 2,746,264; 2,982,112; 3,327,713; 3,826,264; 4,614,191 and 4,646,735.

In medical practice there is a known risk of accidental puncture by used hypodermic needles. Such accidents are particularly problematic with the spread of various infectious diseases, such as AIDS and Hepatitis B, which may be transmitted by infected blood.

SUMMARY OF THE INVENTION

The present invention seeks to provide a needle assembly for medical or veterinary use, which has a needle and a retractable sleeve associated with the needle, so as to reduce the risks of accidental puncture by the needle and of contamination of the exposed needle, and so as also to limit the penetration depth of the needle.

The present invention also seeks to provide a skin piercing device which incorporates a skin piercing element and a desensitizing element, and which, when placed against a portion of skin to be pierced, provides desensitization of the skin so as to render a subsequent introduction into the skin of the piercing element less painful.

A further aim of the present invention is to provide a skin piercing device which incorporates a desensitizing element together with an automatic skin piercing element.

There is thus provided, in accordance with a preferred embodiment of the invention, a needle assembly for medical or veterinary use, and which includes a needle having a needle point, and a sleeve associated with the needle, wherein a predetermined portion of the sleeve has elastic properties in a generally longitudinal direction and is adapted to take up a generally extended state when the assembly is in a non-operative orientation so as to surround the entire length of the needle, and is further adapted to take up a compressed state when the assembly is in an operative orientation, thereby to expose a portion of the needle including the needle point.

Preferably, the portion of the sleeve having elastic properties has the form of either a helical coil or a bellows.

There is also provided, in accordance with a further preferred embodiment of the invention, apparatus for piercing skin including skin piercing apparatus, and a cooling assembly providing a cooled surface associated with the skin piercing apparatus for cooling a portion of skin prior to and during piercing thereof by the skin piercing apparatus.

Additionally in accordance with a preferred embodiment of the invention, the cooling assembly includes a thermoelectric cooling assembly.

Alternatively, the cooling assembly may be a replaceable cooling element adapted to be cooled independently of the apparatus for piercing skin, or fluid cooled apparatus.

Additionally in accordance with a preferred embodiment of the invention, the thermoelectrically cooled surface defines an aperture through which the skin piercing apparatus extends.

In accordance with one embodiment of the invention, the skin piercing apparatus includes a hypodermic syringe.

In accordance with an alternative embodiment of the invention, there is also provided syringe flexible cover apparatus for protecting the needle of the syringe, wherein the cover apparatus is also operative to center the needle along a predetermined axis.

Further in accordance with a preferred embodiment of the invention, there is also provided a housing for the skin piercing apparatus and for the thermoelectric cooling assembly, a shaft mounted in a predetermined orientation in the housing; and means for decouplably attaching the hypodermic syringe to the shaft such that the hypodermic syringe has a predetermined orientation relative to the shaft.

There may also be provided apparatus for automatically operating the hypodermic syringe.

In accordance with an alternative embodiment of the invention, the skin piercing apparatus includes skin pricking apparatus.

Additionally in accordance with a preferred embodiment of the invention, the skin pricking apparatus includes a needle, a needle holder, apparatus for driving the needle through the aperture, and apparatus for preventing accidental driving of the needle through the aperture.

Further in accordance with a preferred embodiment of the invention, there is also provided apparatus for centering the needle along a predetermined axis extending through the aperture.

Additionally in accordance with a preferred embodiment of the invention, there is also provided apparatus for automatically loading the first elastic element and for releasing the first elastic element, thereby to urge the needle holder toward and to drive the needle through the aperture.

Further in accordance with a preferred embodiment of the invention, the skin pricking apparatus is enclosed within a housing which defines a pricking location adjacent to the aperture, and the apparatus also includes apparatus for feeding to the pricking location and for removing therefrom a plurality of needle modules, each including at least a needle and a needle holder.

According to yet a further alternative embodiment of the invention, the skin piercing apparatus is a jet injection device.

BRIEF DESCRIPTION OF THE DRAWINGS

The present invention will be more fully understood and appreciated from the following detailed description, taken in conjunction with the drawings, in which:

FIGS. 4A and 4B are side-sectional views of an end portion of a syringe which has mounted thereon the needle assembly of FIG. 3, in non-operative and operative orientations, respectively;

FIGS. 5A and 5B are schematic side view illustrations of a manually operated hypodermic injection device constructed and operative in accordance with an additional embodiment of the invention, in respective nonoperative and operative positions;

FIGS. 6A and 6B are schematic side view illustrations of an automatic hypodermic injection device constructed and operative in accordance with an embodiment of the invention, in respective nonoperative and operative positions;

FIGS. 17A and 17B are pictorial views of externally cooled cooling apparatus, constructed in accordance with a further embodiment of the present invention, in respective non-operable and operable positions;

FIG. 18 is a pictorial view of a portion of fluid cooled cooling apparatus, constructed in accordance with an additional embodiment of the present invention;

DETAILED DESCRIPTION OF THE INVENTION

Figure 2:
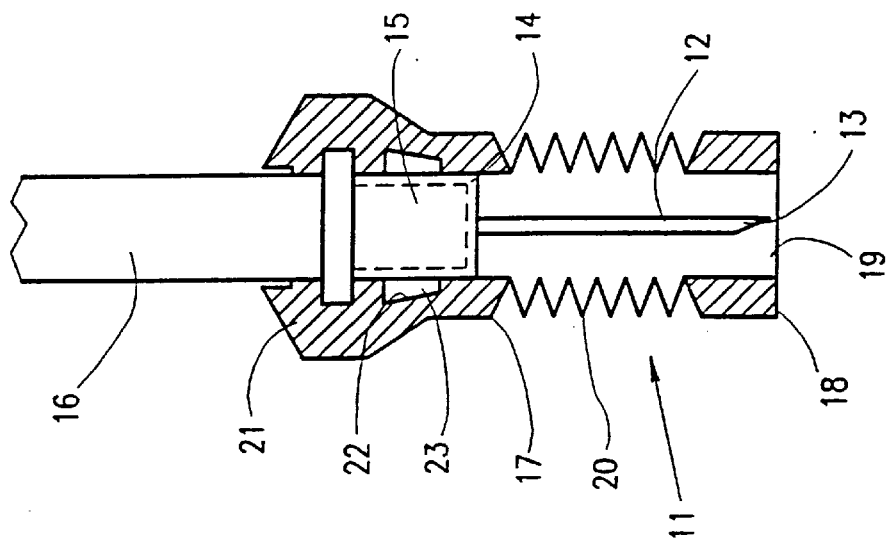
FIG. 2 is a side cross-sectional view of an end portion of a syringe which has mounted thereon the needle assembly of FIG. 1.
Figure 1:
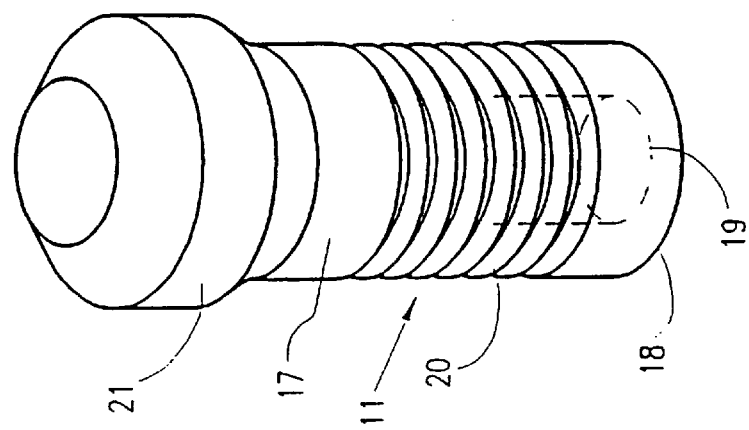
FIG. 1 is a perspective view of a needle assembly constructed in accordance with an embodiment of the invention.

Reference is made to FIGS. 1 and 2, in which are illustrated a needle assembly, referenced generally 11, which includes a hypodermic needle 12 (FIG. 2 only) having a pointed end 13 and an integral needle hub 14 adapted for mounting onto an outlet end 15 of a syringe 16. Assembly 11 also includes a sleeve 17 having a free end 18 which defines an opening 19. Sleeve 17 further has a bellows-type flexible portion 20 and a base 21 which is engaged with needle hub 14 via matching recesses 22 and protrusions 23.

In FIG. 2 the needle assembly 11 is seen in a non-operative state, wherein sleeve 17 surrounds the entire length of needle 12, thereby to substantially reduce the risk of accidental puncture by needle point 13. When free end 18 of sleeve 17 is engaged so as to compress the sleeve, needle 12 is exposed via an opening 19 of the sleeve 17. In order to allow smooth compression of the sleeve 17, it may be perforated thereby to allow the escape of air which might otherwise resist such compression.

Figure 3:
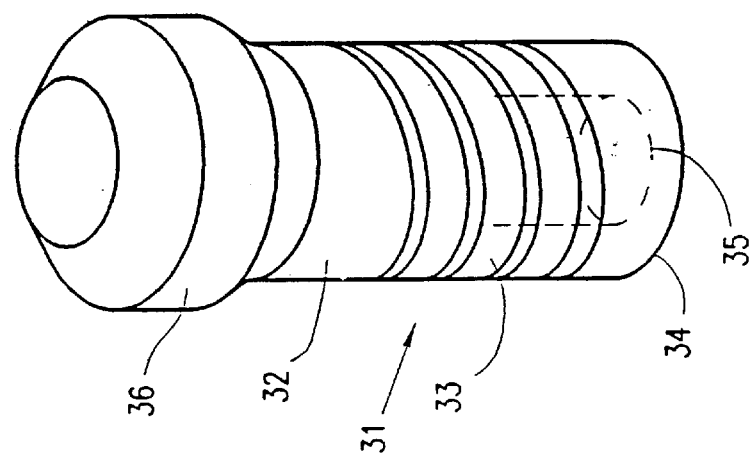
FIG. 3 is a perspective view of a needle assembly constructed in accordance with a further embodiment of the invention.

Reference is now made to FIGS. 3–4B, in which there is illustrated a needle assembly 31 constructed in accordance with a further embodiment of the invention. In FIG. 4A, assembly 31 is illustrated in a non-operational orientation. In FIG. 4B, assembly 31 is illustrated in an operative orientation. Assembly 31 includes a sleeve 32 in the form of a helical coil wherein gaps 33 are provided between adjacent windings. The sleeve 32 has a free end 34 which defines an opening 35, and also has a base 36. Assembly 31 also includes a hypodermic needle 37 (FIGS. 4A and 4B) which has a pointed end 38 and a needle hub 39. The engagement between the needle hub 39 and base 36 of sleeve 32, and the mounting of the needle hub 39 onto an outlet 40 of a syringe 41 are similar to those of the embodiment described hereinabove in conjunction with FIGS. 1 and 2, and thus are not described again herein in detail.

In the non-operative orientation of needle assembly 31 illustrated in FIG. 4A, sleeve 32 surrounds the entire length of the needle and thereby protects against accidental puncture by the needle point 38.

Referring now also to FIG. 4B, in which needle assembly 31 is illustrated in an operative orientation, it is seen that when free end 34 of the sleeve 32 is pressed against skin, illustrated schematically at 45, sleeve 32 becomes compressed, thereby to expose the needle point 38 so as to permit penetration thereof into the skin. The distance "d" between the needle point 38 and the free end 34 of the sleeve 32 in its fully compressed state determines the penetration depth of the needle 37.

After needle 37 has penetrated the skin, a piston 42 of the syringe 41 may be depressed so as to inject a liquid contained in the syringe.

In both of the needle assemblies 11 and 31 illustrated in FIGS. 1–4B, the respective needle hubs 14 and 39 are similar to hubs of prior art hypodermic needles and the assembly may be attached to and removed from a syringe outlet in a manner similar to that of prior art hypodermic needles.

It should be noted that in the above-described embodiments, the sleeve is attached to the needle hub and is intended for one time use together therewith. In an alternative embodiment of the invention, the syringe may be integral with the needle assembly and the sleeve may be attached to the syringe body directly. In this embodiment, the entire needle-syringe assembly is intended to be discarded after a single use.

In accordance with the present invention, the penetration depth of the needle can be adjusted by changing the length of the bellows-type flexible portion 20 (FIGS. 1 and 2), or by changing the number of windings of helical coil 32 or the gap 33 between adjacent windings (FIGS. 3, 4A and 4B).

In order to enable verification of a safe injection, a lower portion of the sleeve may be formed of a transparent material so as to enable a person administering an injection visual access to the needle.

It will be appreciated by persons skilled in the art that the hereinabove described needle assemblies may be modified for blood sampling so as to be used in conjunction with skin pricking apparatus, rather than with a hypodermic syringe.

Needle assemblies constructed in accordance with the above embodiments of the present invention provide significant advantages when used in automatic injection or blood sampling devices. In such devices, it is necessary to control the depth of penetration of the needle. This is known to be provided by a relatively complex mechanism which requires resetting prior to each operation. When using a needle assembly constructed in accordance with the present invention, however, the penetration depth is predetermined by the compressed length of the sleeve and thus no adjustment of the needle assembly is required.

Furthermore, in automatic injection devices, the injection is a two step process. As a first step, the needle is made to penetrate to a predetermined depth and only then is the syringe piston depressed to inject a liquid. By use of the needle assembly of the present invention, the entire injection operation may be a one step process which involves the application of pressure to the piston. By depressing the piston, initially, the relatively flexible sleeve will be compressed against the skin, thereby exposing the needle, which penetrates through the skin. Displacement of the piston relative to the remainder of the syringe will occur only once the sleeve has been fully compressed, thereby ensuring that the injection is made at the desired depth.

Reference is now made to FIGS. 5A and 5B, in which is illustrated a hypodermic injection device, referenced generally 50, constructed and operative in accordance with an embodiment of the invention. In FIG. 5A device 50 is illustrated in a nonoperative position, while in FIG. 5B device 50 is illustrated in an operative position.

Device 50 has a housing 51 in which are mounted a cooling assembly 52 and an injector assembly 53. According to the present embodiment, cooling assembly 52 is a thermoelectric cooling assembly.

According to alternative embodiments of the invention, however, the cooling assembly may be fluid cooled apparatus or externally cooled apparatus, as shown and described hereinbelow in conjunction with FIGS. 17A, 17B and 18.

According to the present embodiment, therefore, thermoelectric cooling assembly 52 typically includes a cooling plate 54, a heat transfer unit 55 thermally connected to cooling plate 54, and a heat sink 57. A fan 58 is preferably also provided for cooling the heat sink 57. Cooling plate 54 has formed therein an aperture 59 and is mounted so to have an exterior surface 60 which is arranged to be in thermally conductive contact with a portion of skin, as illustrated in FIG. 5B.

Injector assembly 53 includes a hypodermic syringe 61 which has a needle 62, a piston 63, and a flexible cover 64 for needle 62. Cover 64 is operative to prevent inadvertent puncture by the needle 62, thereby to perform a function similar to that of sleeve 17 (FIGS. 1 and 2) and sleeve 32 (FIGS. 3, 4A and 4B) described hereinabove. According to the present embodiment, however, cover 64 is made from a resilient material, such as rubber. Syringe 61 is mounted such that needle 62 is in axial registration with aperture 59 of cooling plate 54.

It should be noted that, in an alternative embodiment of the invention, the hypodermic syringe 61 may be replaced by a jet injection device such as shown and described hereinbelow in conjunction with FIG. 19.

According to the present embodiment, housing 51 is configured such that a portion of hypodermic syringe 61 and piston 63 protrude through the wall of the housing. Syringe 61, furthermore, is slidably mounted, via a syringe support member 65, onto a guide 66.

The use of device 50 is now described in conjunction with FIG. 5B:

Initially, cooling assembly 52 is activated, as by a suitable switch device (not shown) so as to cool the cooling plate 54 to a temperature selected to desensitize the skin. Device 50 is then positioned such that the exterior surface 60 of cooling plate 54 contacts a portion of skin, referenced 67. After a period of time selected to desensitize the skin has elapsed, typically in the region of no more than about five seconds, syringe 61 is then displaced manually along guide 66 in the direction of an arrow 68 (FIG. 5B) such that an end portion 69 of the cover 64 of needle 62 engages cooling plate 54 so as to be compressed thereagainst. As the syringe 61 is displaced further, needle 62 emerges via aperture 59 of cooling plate 54 so as to enter the skin to a predetermined depth. Piston 63 may then be depressed so as to cause injection of a liquid contained in the syringe 61. Afterwards, the syringe 61 is withdrawn from the skin and the device 50 may be prepared for reuse.

Figure 5C:
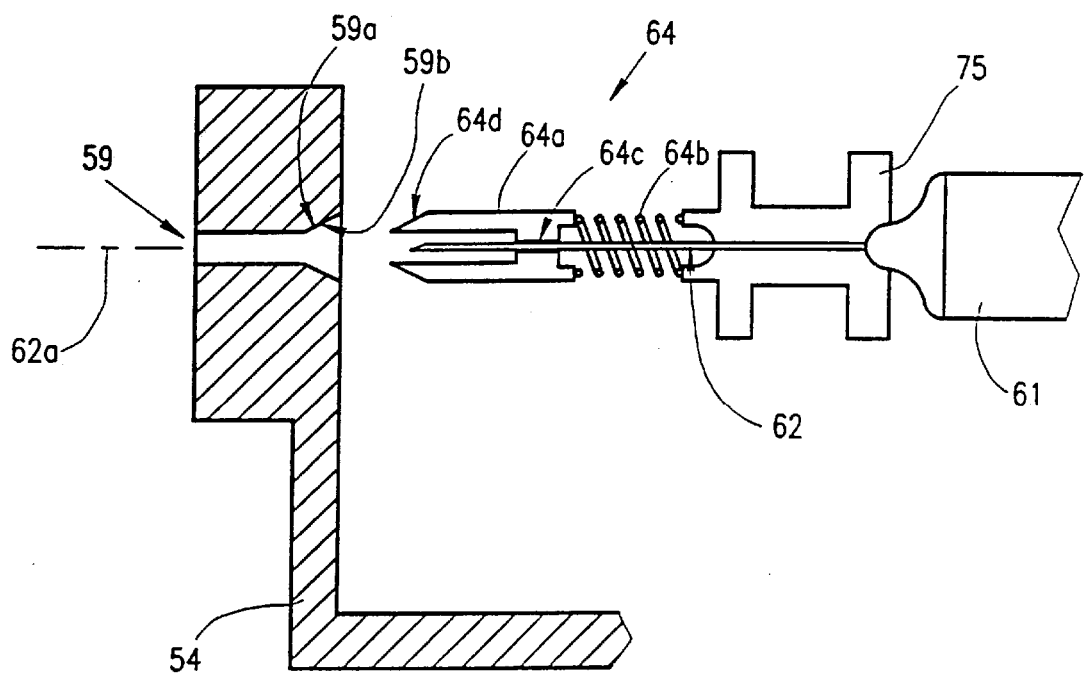
FIG. 5C is a schematic, partially cut-away side view of a portion of the injection device of FIGS. 5A and 5B, constructed in accordance with an alternative embodiment of the invention.

Reference is now made to FIG. 5C, in which is illustrated a portion of injection device 50 (FIGS. 5A and 5B), constructed in accordance with an alternative embodiment of the invention.

As seen in FIG. 5C, the sleeve 64 comprises a generally rigid end portion 64a and a resilient intermediate portion 64b associated with a hub 75 attached to syringe 61. End portion 64b typically contains a helical spring or the like. Cooling plate 54 has an aperture 59 which has a relatively wide, inward-facing, conical end 59a which defines a conical engagement surface 59b. End portion 64a of sleeve 64 has a thickened portion 64c which is configured to engage needle 62 along a predetermined length thereof, such that the needle 62 is aligned along a predetermined axis of movement 62a which is coincident with the axis of symmetry of the sleeve. End portion 64a further has a cone-shaped end 64d which is configured for mating engagement with conical engagement surface 59b.

Accordingly, when syringe 61 is displaced toward cooling plate 54, cone-shaped end 64d of end portion 64a of sleeve 64 engages conical engagement surface 59b of aperture 59, thereby to lock sleeve 64 and, therefore, needle 62 along axis 62a. Further displacement of syringe 61 toward cooling plate 54 causes resilient intermediate portion 64b of sleeve 64 to be compressed, and needle 62 emerges from sleeve 64 via aperture 59, substantially as described above in conjunction with FIGS. 5A and 5B.

It should be noted that the sleeve and aperture configuration of FIG. 5C may be incorporated into any of the syringe devices shown and described herewith.

Figure 6A:
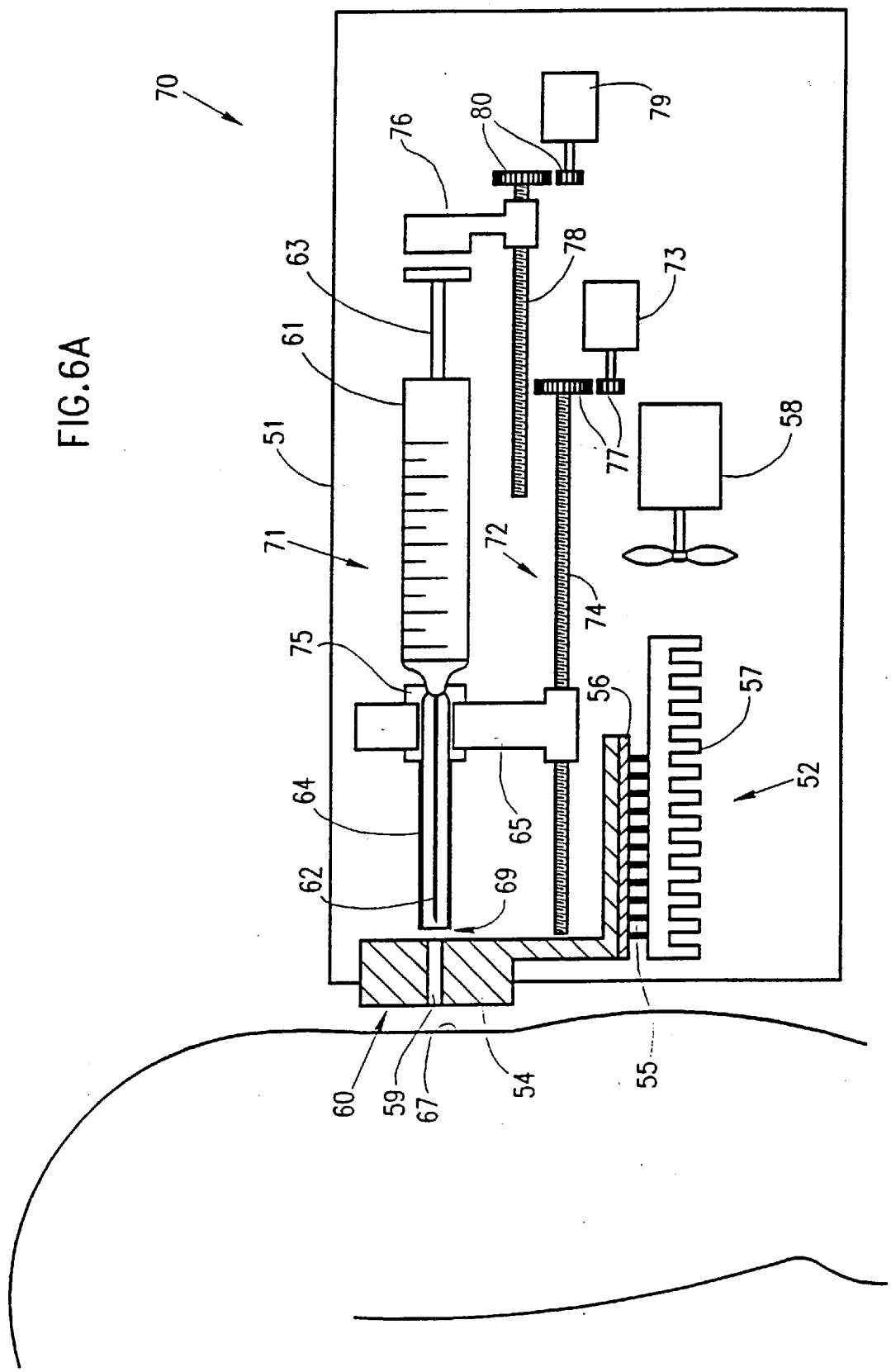

Reference is now made to FIGS. 6A and 6B, in which there is illustrated an automatic hypodermic injection device, referenced generally 70, constructed and operative in accordance with an alternative embodiment of the invention. Device 70 is similar to device 50 (FIGS. 5A and 5B) described above, except that device 70 is operated automatically, as described hereinbelow. Accordingly, components of device 70 that correspond to components of device 50 are denoted by similar reference numerals and are not specifically described again herein.

According to the present embodiment, there is provided an automatic injector assembly 71 which is similar to injector assembly 53, but which also includes a syringe actuator and support 72, and a first motor 73. Syringe actuator and support 72 includes an axially rotatable first drive shaft 74 mounted so as to be generally parallel to the syringe 61.

The syringe 61 is supported on first drive shaft 74 via hub 75 and a syringe support member 65. Syringe support member 65 is internally threaded so as to be threadably mounted onto first drive shaft 74. An internally threaded piston engagement member 76 is threadably mounted onto a second drive shaft 78. Second drive shaft 78 is operative to drive piston engagement member 76 therealong, via a second motor 79 and second gears 80, thereby to engage and depress piston 63 of syringe 61.

The use of device 70 is now described in conjunction with FIG. 6B:

Initially, cooling assembly 52 is activated, as by a suitable switch device (not shown) so as to cool the cooling plate 54 to a temperature selected to desensitize the skin.

After a predetermined period of time has passed, typically no more than about five seconds, device 70 is positioned such that the exterior surface 60 of cooling plate 54 contacts a portion of skin, referenced 67.

Subsequently, first motor 73 of injector assembly 71 is activated via a switch (not shown) so as to cause an axial rotation of first drive shaft 74 via first gears 77, thereby to displace syringe support member 65 and syringe 61 therealong toward cooling plate 54.

As the syringe 61 continues to be moved towards the cooling plate 54, an end portion 69 of the cover 64 of needle 62 engages cooling plate 54 so as to be compressed thereagainst. As the syringe is displaced further along first drive shaft 74, needle 62 emerges from housing 51 through aperture 59 so as to protrude therefrom by a distance which corresponds to a predetermined injection depth.

Second motor 79 is operated to drive piston engagement member 76 toward piston 63 via second gears 80 and second drive shaft 78, such that once needle 62 is at a position of maximum extension through aperture 59, piston engagement member 76 is operative to engage and depress piston 63, thereby to cause injection of a liquid contained in the syringe.

Once piston 63 has been completely depressed, the directions of first motor 73 and second motor 79 are reversed so as to reverse the directions of rotation of first and second drive shafts 74 and 78. This reverse rotation of the first and second drive shafts 74 and 78 causes syringe support member 65, syringe 61, and piston engagement member 76 to be returned to their non-operative positions as seen in FIG. 6A.

Figure 7:
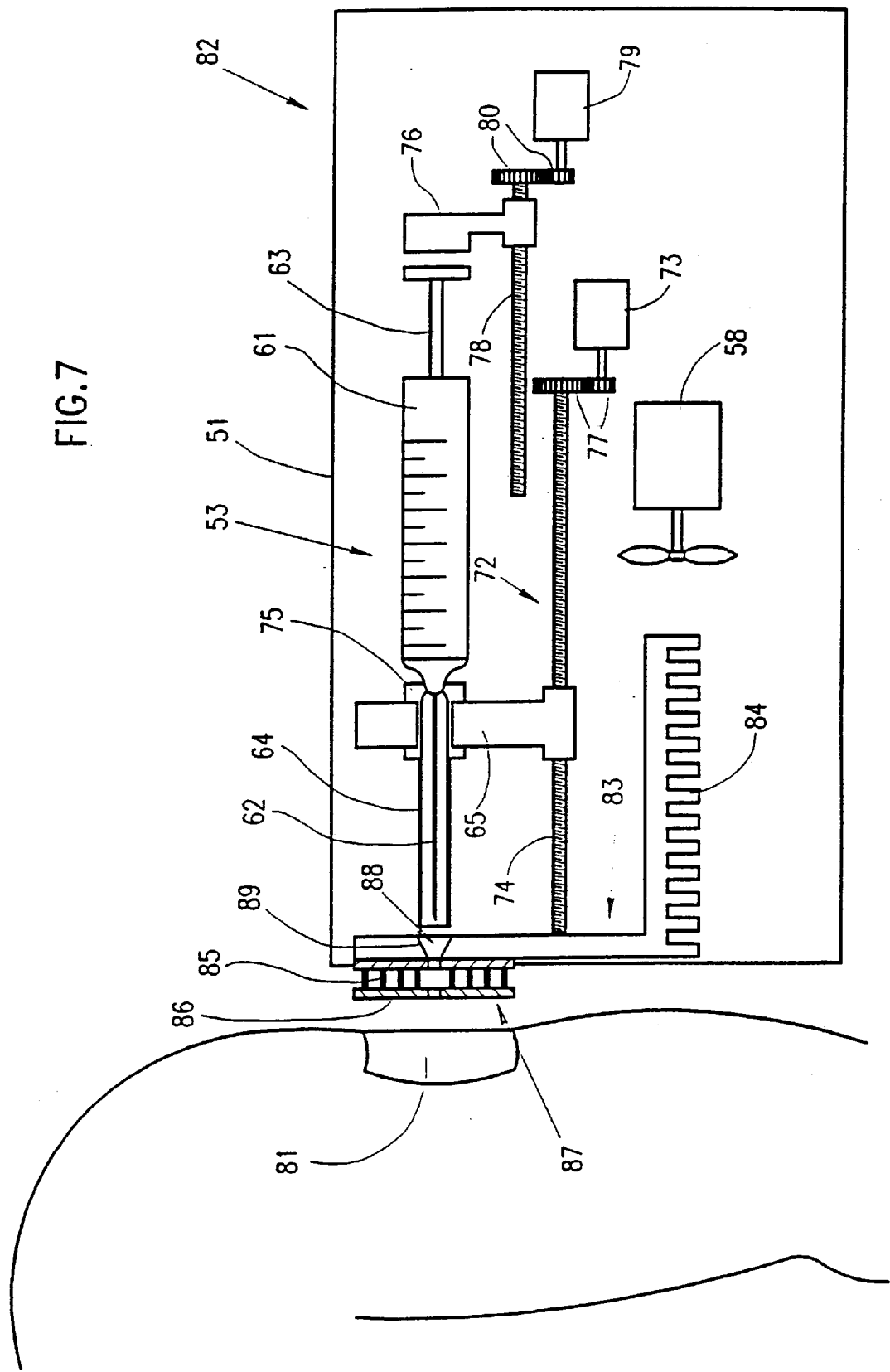
FIG. 7 is a schematic side view illustration of an automatic hypodermic injection device constructed and operative in accordance with an alternative embodiment of the invention.

Reference is now made to FIG. 7, which is an illustration of an automatic hypodermic injection device 82 constructed and operative in accordance with a further embodiment of the invention. Device 82 is similar to device 70 (FIGS. 5A and 5B) described above, except that device 82 employs a thermoelectric cooling assembly 83 that is different from that used in device 70, as will be understood from the following description. Accordingly, components of device 82 that correspond to components of device 70 are denoted by similar references numerals and are not specifically described again herein.

Cooling assembly 83 includes a heat sink 84, a heat transfer unit 85 and a cooling plate 86. Heat transfer unit 85 and cooling plate 86 are arranged so as to protrude externally of housing 51 such that cooling plate 86 is used as a cold surface for directly contacting and cooling skin.

According to the present embodiment, cooling assembly 83 is arranged across the path of the needle 62 and has formed therein an aperture 87 which extends through all the components of the cooling assembly.

Additionally in accordance with the present embodiment, aperture 87 is configured to have a relatively wide, conical end 88 disposed inwardly of the housing 51 and facing needle 62. Accordingly, even if the needle 62 is not properly aligned, or is slightly bent, engagement thereby of a conical surface 89 at aperture end 88 will cause the needle to be correctly aligned.

If desired, a sterile thin layer 81 of a material formed of thermally conductive material may be placed on the patient's skin, so as to avoid skin contact with an unsterilized cooling plate. Layer 81 may be attached to the skin with adhesive.

Figure 8:
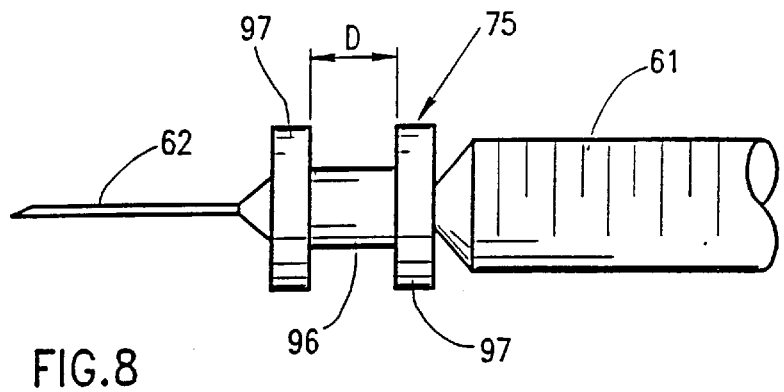
FIG. 8 is an enlarged side view of an end portion of a hypodermic syringe employed in the devices of FIGS. 5A–7.
Figure 9A:
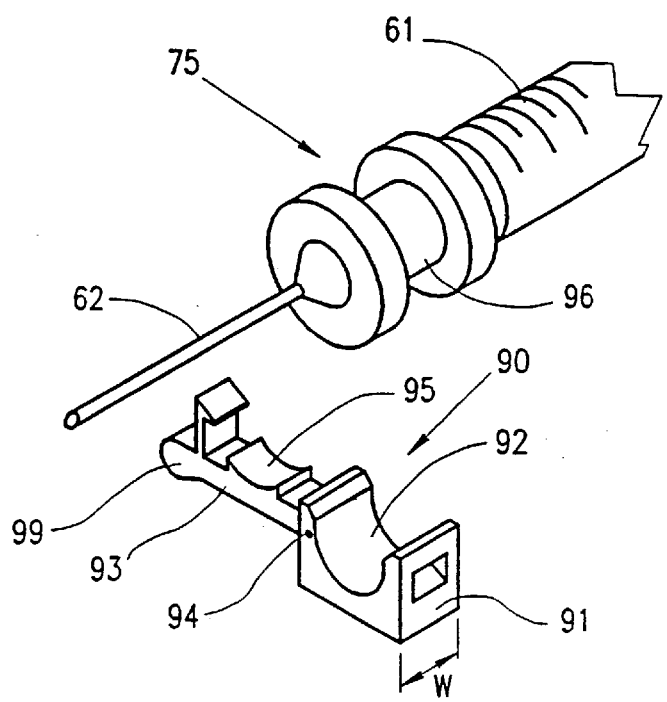
FIGS. 9A and 9B are pictorial illustrations of an end portion of the hypodermic syringe depicted in FIG. 8, prior to and during engagement with a syringe support member constructed in accordance with a further alternative embodiment of the invention.
Figure 9B:
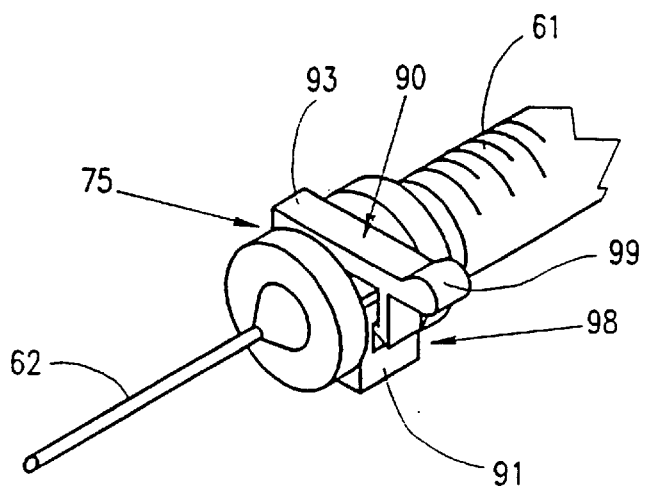

Reference is now made to FIG. 8, in which an end portion of syringe 61 (FIGS. 5A–7) is illustrated, and to FIGS. 9A and 9B, in which are illustrated hub 75 and a syringe support member 90 adapted for use therewith. According to the present embodiment of the invention, syringe support member 90 is adapted for use in place of syringe support member 65 (FIGS. 5A–7). Syringe support member 90 includes a base portion 91 in which is formed a recess 92, and a locking member 93 mounted onto base portion 91 via a hinge 94. Locking member 93 includes a hub engagement surface 95.

As seen in FIG. 8, hub 75 is formed so as to define an intermediate portion 96 surrounded by a pair of end portions 97. End portions 97 are preferably spaced apart by a distance "D" that is similar to the width "W" of base portion 91, such that engagement of hub 75 with the syringe support member 90 provides accurate positioning of the syringe 61 relative to its support.

Once syringe 61 has been placed such that intermediate portion 62 of hub 75 is seated in recess 92 of base portion 91, locking member 93 may be closed such that hub engagement surface 95 engages intermediate portion 96 so as to lock hub 75 and, therefore, the syringe 61, into a required position. Locking member 93 may be fastened to base portion 91 via a suitable openable locking mechanism 98. In the present example, locking mechanism 98 is a snap-type mechanism. A handle 99 may also be provided for enabling convenient manual opening of syringe support member 90, thereby to facilitate easy replacement of the syringe 61.

Figure 10B:
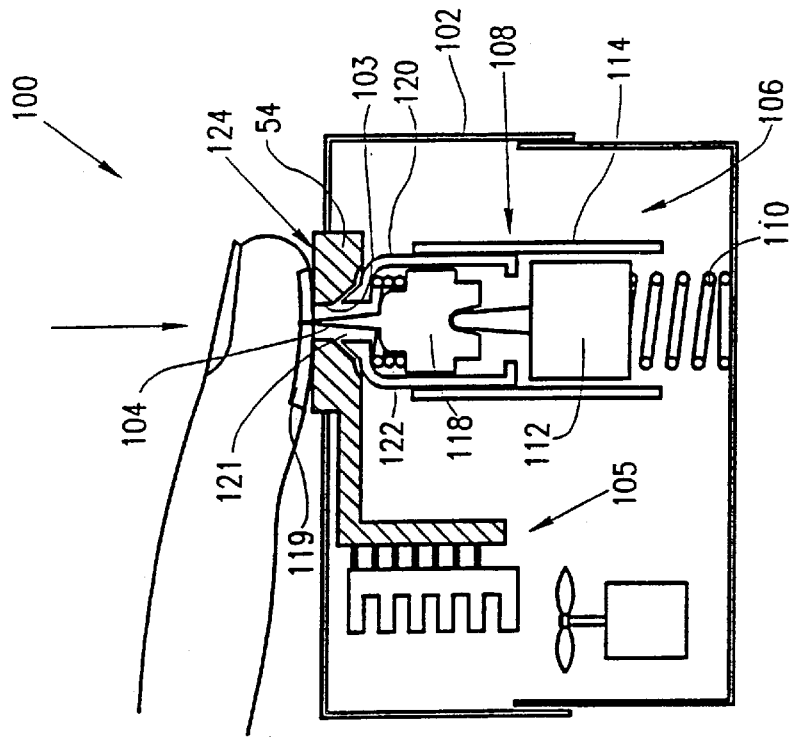
FIGS. 10A and 10B are schematic side view illustrations of a manually operated pricking device constructed and operative in accordance with an embodiment of the invention, in respective nonoperative and operative positions.
Figure 10A:
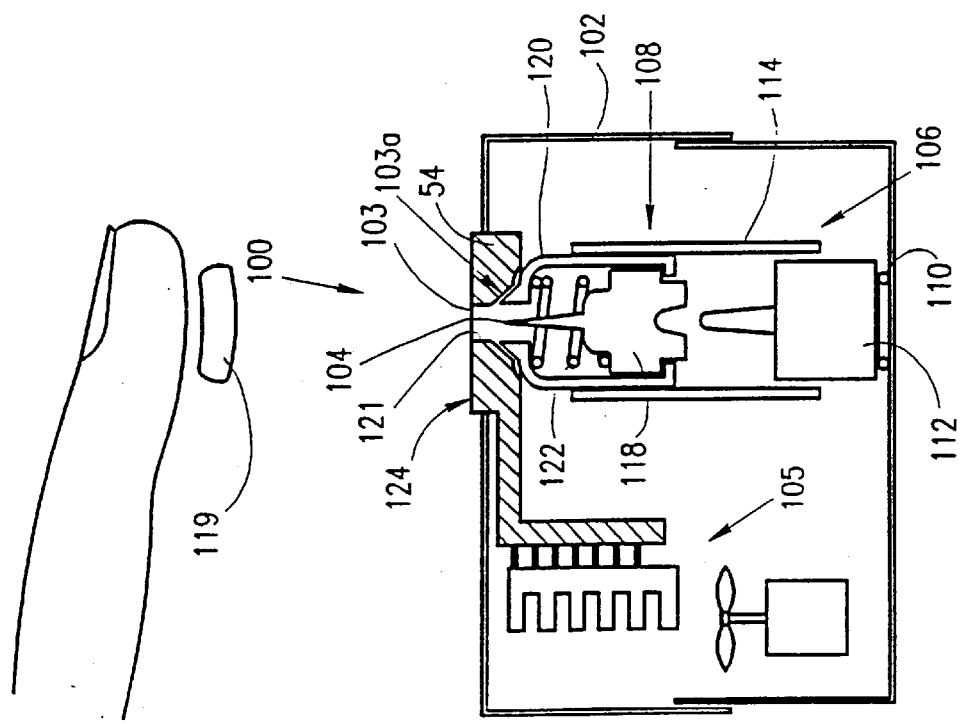

Reference is now made to FIGS. 10A and 10B, in which is illustrated a manually operated pricking device, referenced generally 100, constructed and operative in accordance with an embodiment of the invention, in respective nonoperative and operative positions. Pricking device 100 is typically used for lancing or the like. Device 100 includes a housing 102 in which are mounted a cooling assembly 105 and a manually operated pricking assembly 106.

Although cooling assembly 105 may be any type of suitable cooling apparatus, it is typically a thermoelectric cooling assembly similar to the cooling assembly 52 of device 50, shown and described hereinabove in conjunction with FIGS. 5A and 5B, and is thus not specifically described again herein. As seen in the drawings, cooling plate 54 which forms part of thermoelectric cooling assembly 105 has formed therein an opening 103 through which a needle 104 extends during pricking operations.

If desired, a sterile thin layer 119 of a material formed of thermally conductive material may be placed on the patient's skin, so as to avoid skin contact with an unsterilized cooling plate. Layer 119 may be attached to the skin with adhesive.

Figure 11B:
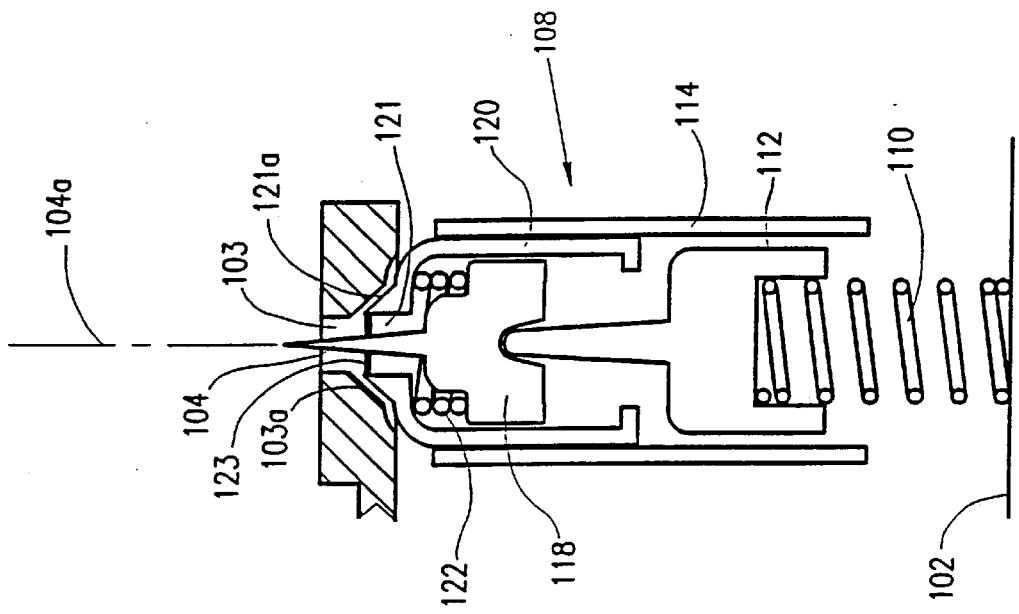
FIGS. 11A and 11B are schematic side view illustrations of the needle module employed in the device of FIGS. 10A and 10B, in respective nonoperative and operative positions.
Figure 11A:
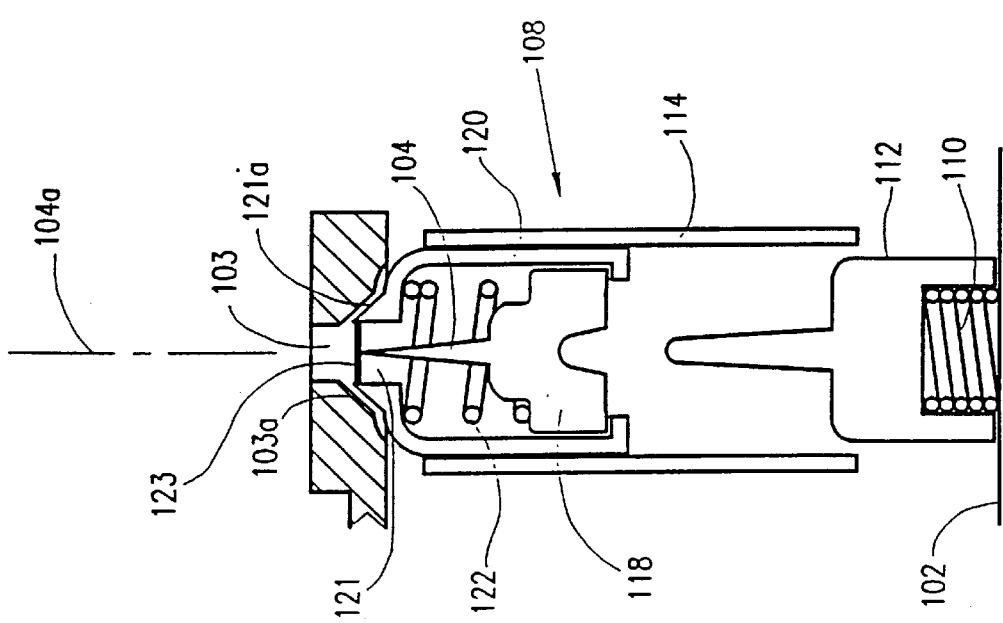

Referring now also to FIGS. 11A and 11B, according to the present embodiment, it is seen that the manually operated pricking assembly 106 includes a needle module 108 that is mounted, via a first compression spring 110, onto a portion of the housing 102. Needle module 108 includes a force transfer element 112 mounted onto the first spring 110 and housed within a leader member 114 arranged within the housing 102.

Needle module 108 further includes a needle 104, a needle holder 118, a needle housing 120 having a needle aperture 121 and a conical end portion 121a, and a second compression spring 122. Needle module 108 is arranged within housing 102 such that needle aperture 121 is in registration with opening 103 so as to permit exposure therethrough of the needle 104, thereby to enable pricking. Opening 103 defines an inward-facing conical surface 103a which is adapted for engagement by conical end portion 121a of needle housing, thereby to ensure that needle holder 118 and, therefore, needle 104, is maintained in alignment with an axis of motion 104a, which coincides with the axis of symmetry of the needle housing 120.

In an at rest position, illustrated in FIGS. 10A and 11A, second compression spring 122 retains needle holder 118 and, therefore, needle 104 in a retracted position relative to aperture 121, thereby preventing accidental pricking. An easily pierced cap member 123 may be located at the forward end of needle housing 120 for wiping the needle 104 as it passes thereby preventing liquid contact between the needle 104 and the opening 103, thus preserving sterility of the needle even when the cooling plate is not sterile.

In operation, device 100 is brought into contact with a portion of skin, typically of a finger (FIG. 10B), such that the skin touches a cool surface 124 of cooling plate 54 of the cooling assembly 105. After a short time has elapsed to allow cooling sufficient to desensitize the skin, force transfer element 112 is manually displaced downward against the first compression spring 110 to the position illustrated in FIGS. 10A and 11A.

Release of the force transfer element 112 enables first compression spring 110 to urge it into engagement with needle holder 118, so as to force needle holder 118 and needle 104 in a generally upward direction, thereby to cause needle 104 to pierce cap member 123 and to emerge through aperture 121 and opening 103, so as to prick an adjacent portion of skin. As needle holder 118 is urged upwardly, as described, second compression spring 122 is compressed.

Although second compression spring 122 is selected to be weaker than first compression spring 110, it is nonetheless strong enough so as to assist return of the needle holder to a retracted position within the housing 102 after the required pricking has been provided.

Reference is now made to FIGS. 12A, 12B, 13 and 14, in which are illustrated portions of an automatic pricking device, referenced generally 130, constructed and operative in accordance with a further alternative embodiment of the invention.

Figure 12A:
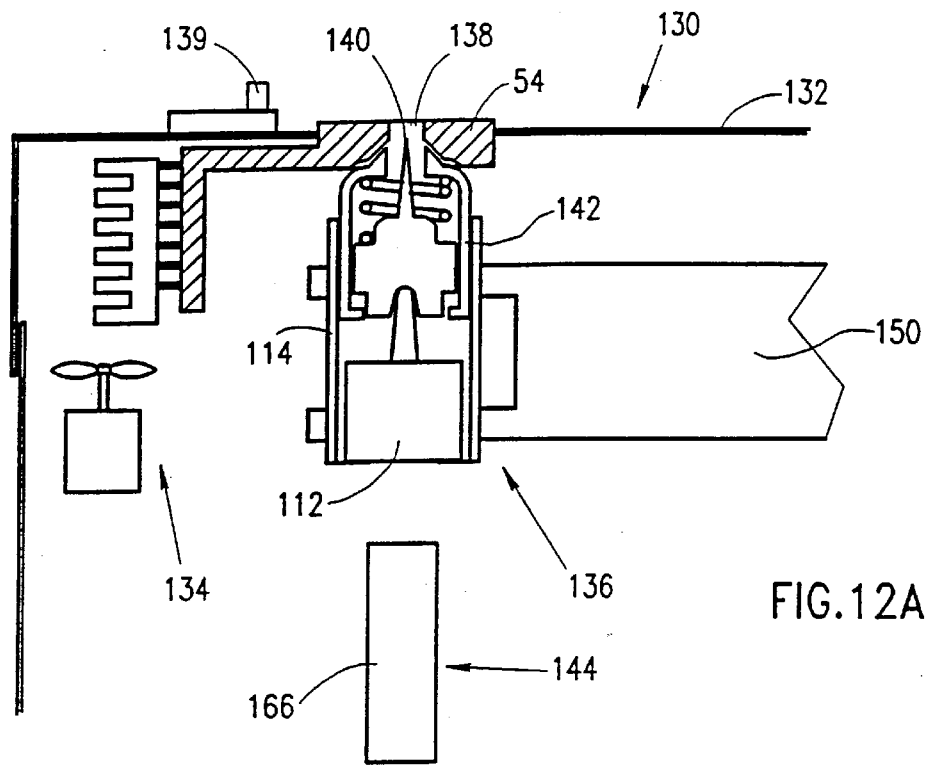
FIGS. 12A and 12B are schematic side view illustrations of a portion of an automatic pricking device constructed and operative in accordance with an additional embodiment of the invention, taken in the direction of arrow 12 in FIG. 13 in respective nonoperative and operative positions.
Figure 12B:
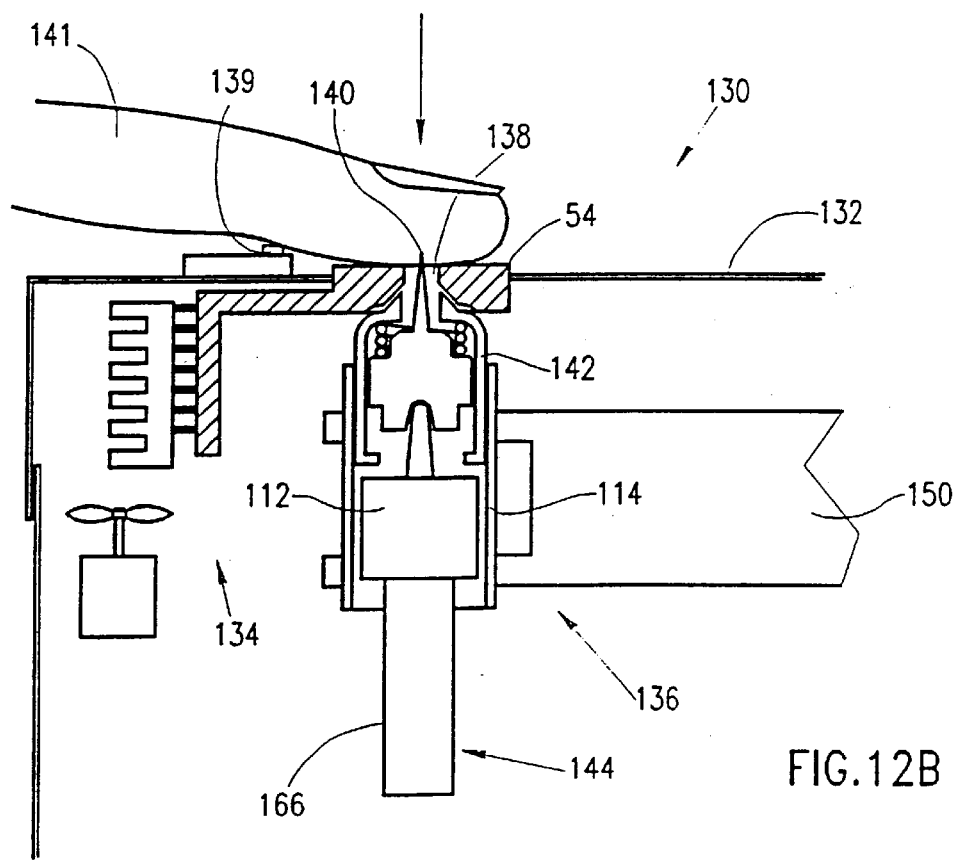

Referring initially to FIGS. 12A and 12B, it is seen that device 130 includes a housing 132 in which are mounted a cooling assembly 134 and an automatic pricking assembly 136. Cooling assembly 134 is generally similar to the cooling assembly 52 of device 50, shown and described hereinabove in conjunction with FIGS. 5A and 5B, and is thus not specifically described again herein.

As seen in the drawings, cooling plate 54 which forms part of thermoelectric cooling assembly 134 has formed therein an opening 138 through which a needle 140 extends during pricking operations. In the present embodiment, the device 130 is activated via an electrical switch 139 that is mounted onto the housing 132 adjacent to the cooling plate 54. Switch 139 is adapted to activate device 130 when depressed by a finger 141 placed over cooling plate 54, as illustrated in FIG. 12B.

According to an alternative embodiment, however, cooling assembly 134 of device 130 may be operable in response to sensing of skin contact with cooling plate 54, substantially as described hereinabove in conjunction with cooling assembly 105. (FIGS. 10A and 10B).

In accordance with the illustrated embodiment of the invention, automatic pricking assembly 136 includes a needle module 142 that is generally similar to needle module 108 described above in conjunction with FIGS. 12A ad 12B, except that force transfer element 112 is contained completely within leader member 114. An upward displacement of force transfer element 112 is provided by activation of a spring mounted hammer 144, substantially as described below in conjunction with FIGS. 13–16B.

Figure 13:
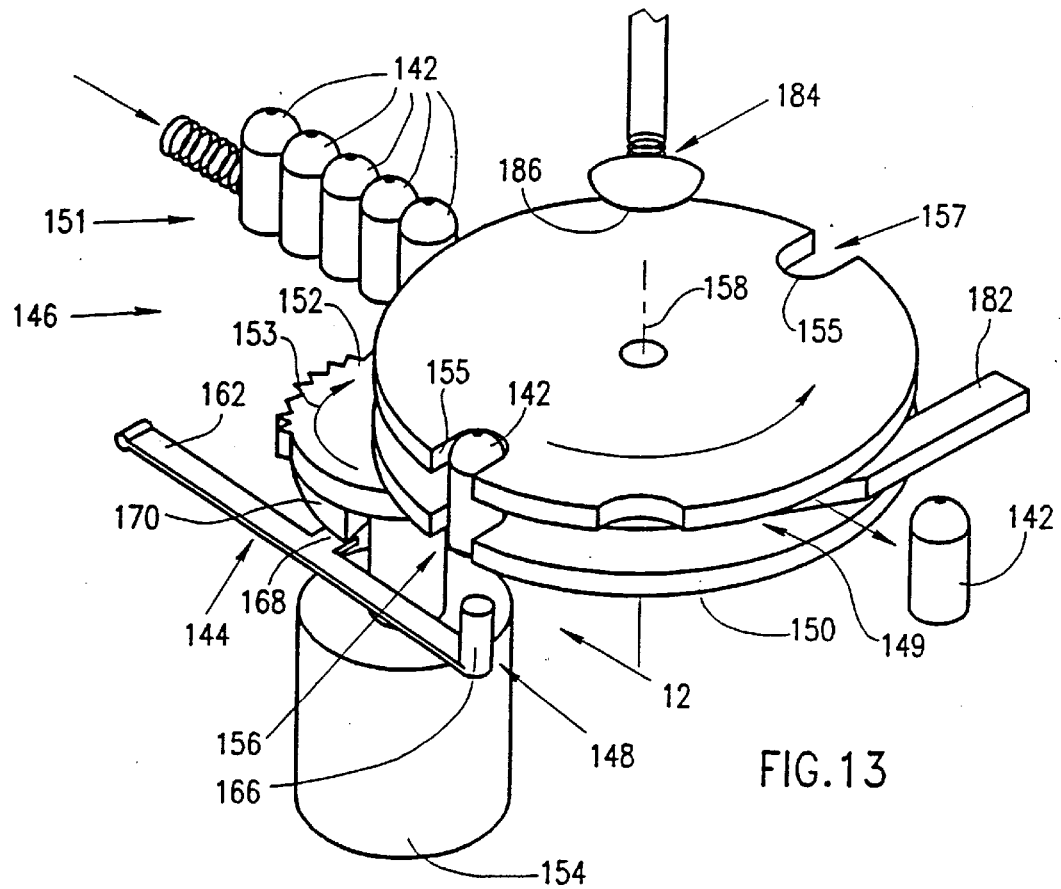
FIG. 13 is a pictorial illustration of a feed and ejector assembly of the pricking device of FIGS. 12A and 12B.
Figure 14:
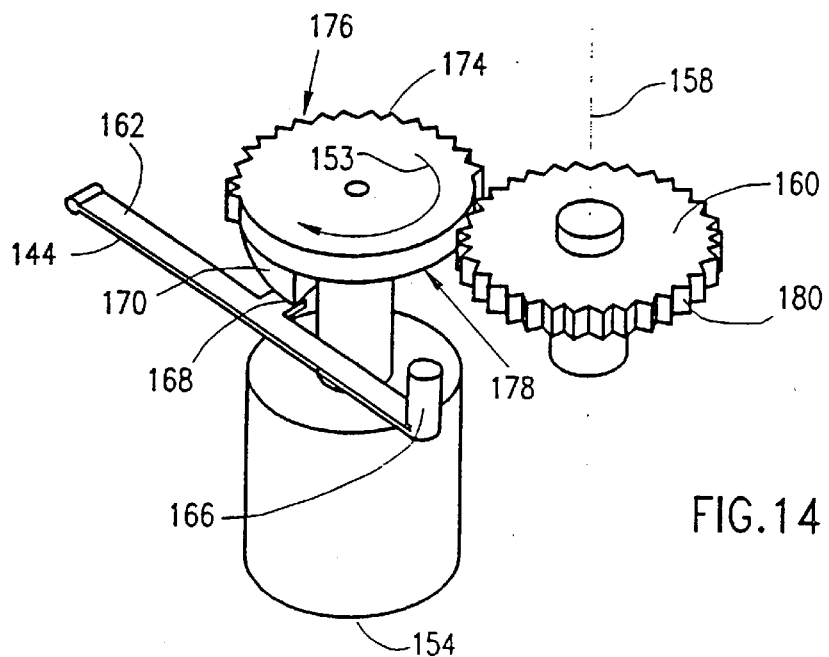
FIG. 14 is a pictorial illustration of a drive assembly forming part of the assembly illustrated in FIG. 13.

Referring now to FIG. 13, it is seen that device 130 has an assembly, referenced generally 146, for feeding needle modules 142 to a pricking location, referenced generally 148, and for ejecting used modules. Assembly 146 includes a needle module feed drum 150, a drive wheel 152, a motor 154 for drive wheel 152 and hammer 144.

Feed drum 150 is adapted to receive needle modules 142 from a cartridge, indicated schematically at 151, and to seat a single needle module 142 in each of first and second recesses 156 and 157. Feed drum 150 is arranged for rotation about a rotation axis 158 via drive wheel 152 and a gear wheel 160 (FIGS. 14, 15B and 16B), thereby to convey a needle module 142 first, to pricking location 148 and subsequently, after a pricking operation, to an ejection location 149.

Referring now also to FIGS. 14–16B, it is seen that hammer 144 includes a shaft 162 and a hammerhead 166 which is adapted for engaging force transfer element 112 (FIGS. 12A and 12B). Shaft 162 is attached to a fixed support 163 via a resilient compression member 164 (FIGS. 15A and 16A), such as a helical spring. Shaft 162 also has a cam follower 168 which is adapted for engagement by a cam 170 formed on a bottom surface of drive wheel 152. Rotation of drive wheel 152 causes a corresponding rotation of cam 170 in engagement with cam follower 168. As drive wheel 152 and cam 170 rotate, thereby displacing hammer 144, compression member 164 becomes elastically loaded. The loading reaches a maximum when the cam follower 168 is engaged by an edge portion 172 of cam 170.

As drive wheel 152 continues to rotate such that cam 170 moves suddenly out of engagement with cam follower 168, the hammer is released such that hammerhead 166 forcibly engages force transfer element 112 (FIGS. 12A and 12B) of needle module 142, thereby to operate the needle module 142 substantially as described above in conjunction with needle module 108 of device 100 (FIGS. 10A and 10B).

Drive wheel 152 is preferably formed with teeth 174 along a predetermined first peripheral portion 176. A second peripheral portion 178 is smooth. It will be appreciated that rotation of feed drum 150 occurs only when teeth 180 of gear wheel 160 are in driven engagement with teeth 174 of drive wheel 172.

In operation of device 130, motor 154 rotates drive wheel 152 in a direction indicated by an arrow 153 so as to cause a displacement of hammer 144 thereby to load compression member 164. At this stage, a needle module 142 is held at pricking location 148 via first recess 156 of drum 150. At this stage, as teeth 174 of drive wheel 152 are not drivingly engaged with teeth 180 of gear wheel 160, drum 150 remains stationary so as to retain needle module 142 at pricking location 148.

Figure 15A:
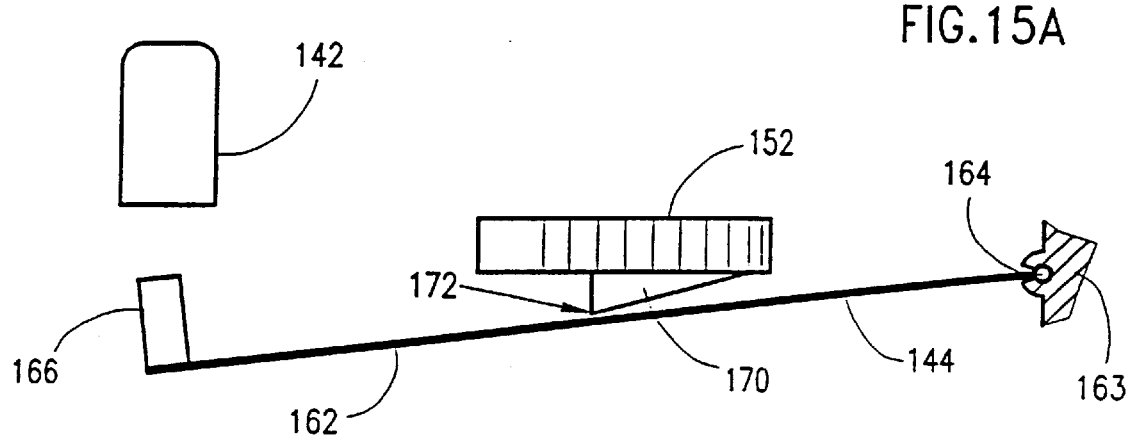
FIGS. 15A and 15B are respective side and top views of the drive assembly of FIG. 14 prior to operative engagement with a needle module of FIG. 13.
Figure 15B:
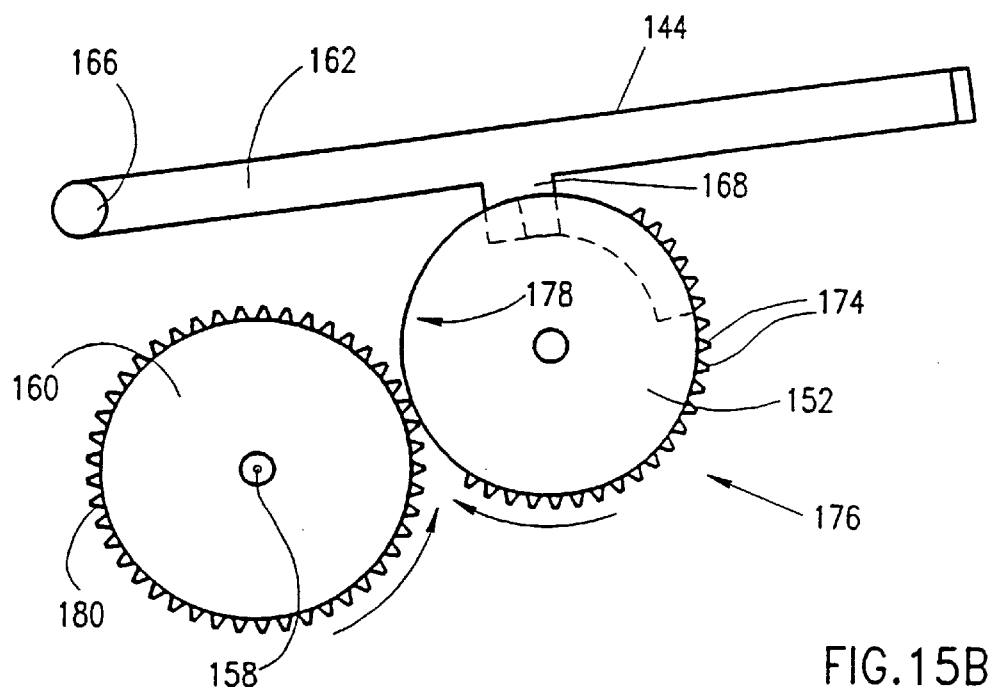
Figure 16A:
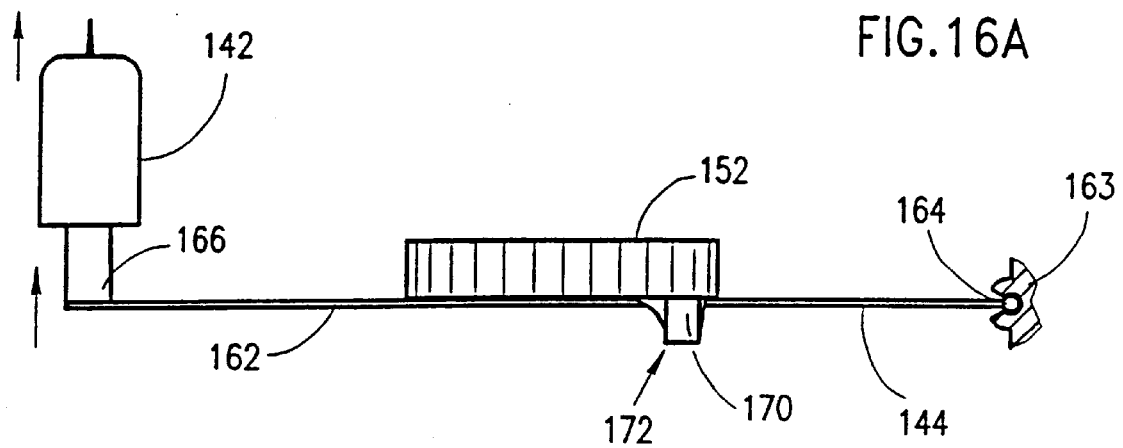
FIGS. 16A and 16B are respective side and top views of the drive assembly of FIG. 14 during operative engagement with a needle module of FIG. 13.
Figure 16B:
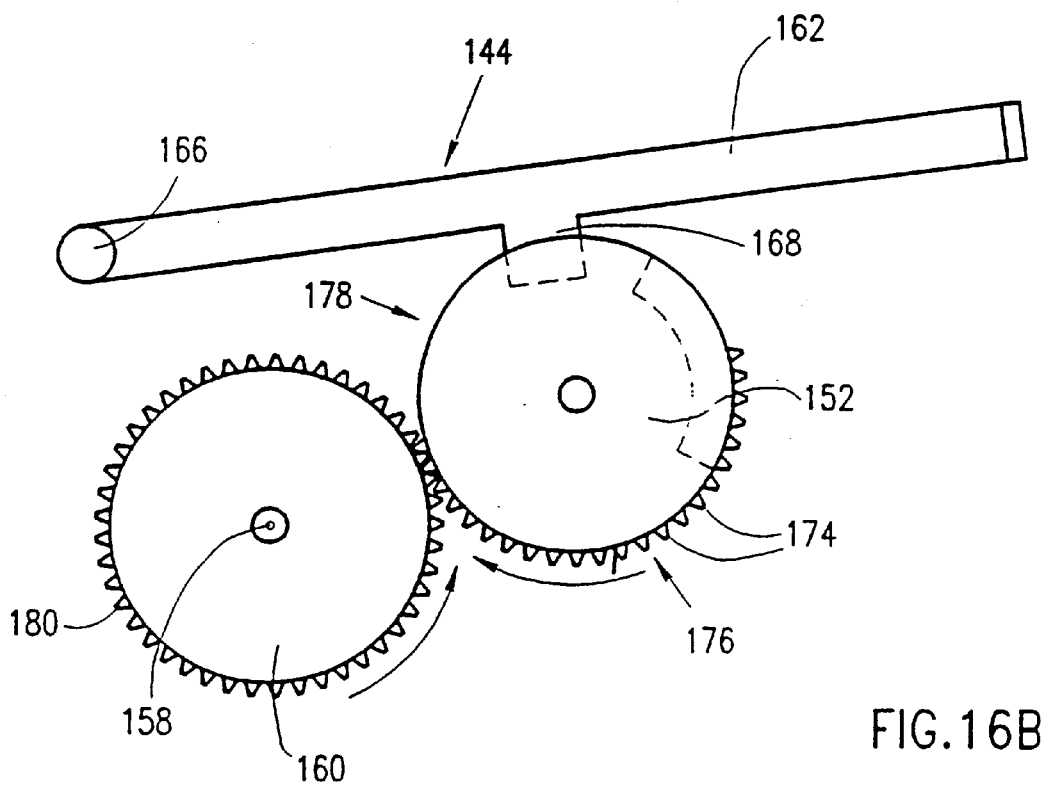

When drive wheel 152 has rotated such that cam follower 168 is engaged by edge portion 172 of cam 170, as illustrated in FIGS. 15A and 15B, a further slight rotation thereof is operative to release hammer 144, as illustrated in FIG. 16A. Release of the loaded hammer 144 permits a return displacement thereof towards needle module 142. The return displacement of hammer 144 causes a forcible displacement thereby of the force transfer element 112 of the needle module 142 so as to cause operation thereof in a manner similar to that of needle module 108 (FIGS. 10A and 10B).

Subsequently, drive wheel 152 continues to rotate until teeth 174 thereof drivingly engage teeth 180 of gear wheel 160, thereby to cause rotation of feed drum 150. As feed drum 150 rotates, the used needle module 142 is engaged by an ejector arm 182, thereby to cause ejection and discarding of the used module. At the same time, second recess 157 is brought into registration with cartridge 151 so as to receive a fresh needle module.

Feed drum 150 continues to rotate until second recess 157 and the fresh needle module 142 are brought into registration with the pricking location 148, at which time a limit switch (not shown) is activated at this time so as to deactivate motor 154, and a positioning mechanism 184 (FIG. 13) is operative to halt rotation of the drum 150 completely.

In the present example, positioning mechanism 184 comprises a spring-loaded bearing acting in conjunction with a peripheral depression 186 formed in drum 150. In other embodiments, however, a positioning mechanism may be constituted by any suitable means.

Reference is now made to FIGS. 17A and 17B in which is seen cooling apparatus, referenced generally 200, suitable for use in any of the syringe or pricking devices shown and described hereinabove. Cooling apparatus 200 comprises a removable cooling plate 202 which is adapted for cooling by external means, such as a refrigerator or freezer. Preferably, cooling plate 202 is made from a material having high thermal conductivity and high thermal capacity.

Cooling plate 202 defines an opening 204 and is adapted for removable mounting in a holder 206 located in a housing 208 such that opening 204 is in axial registration with a needle 210. Needle 210 may be a hypodermic needle or a pricking needle as described hereinabove, or it may alternatively be replaced by a jet injection device, substantially as shown and described hereinbelow in conjunction with FIG. 19.

Cooling plate 202 is typically formed with depressions 212 which are adapted to engage protrusions 214 of holder 206 so as to be supported therein. Cooling plate 202 may thus be made for sliding engagement with holder 206 or, if the holder 206 is made from a suitable type of plastic, the cooling plate 202 may be made for a snap-type engagement therewith.

Reference is now made to FIG. 18 in which is seen cooling apparatus, referenced generally 220, suitable for use in any of the syringe or pricking devices shown and described hereinabove. Cooling apparatus 220 comprises a fluid cooled cooling element 222, through which a suitable refrigerant fluid is passed via inlet and outlet conduits, referenced 226 and 227, respectively.

Cooling element 222 defines an opening 224 and is positioned in a housing 228 such that opening 224 is in axial registration with a needle 229. Needle 229 may be a hypodermic needle or a pricking needle as described hereinabove, or it may alternatively be replaced by a jet injection device, substantially as shown and described hereinbelow in conjunction with FIG. 19.

Figure 19:
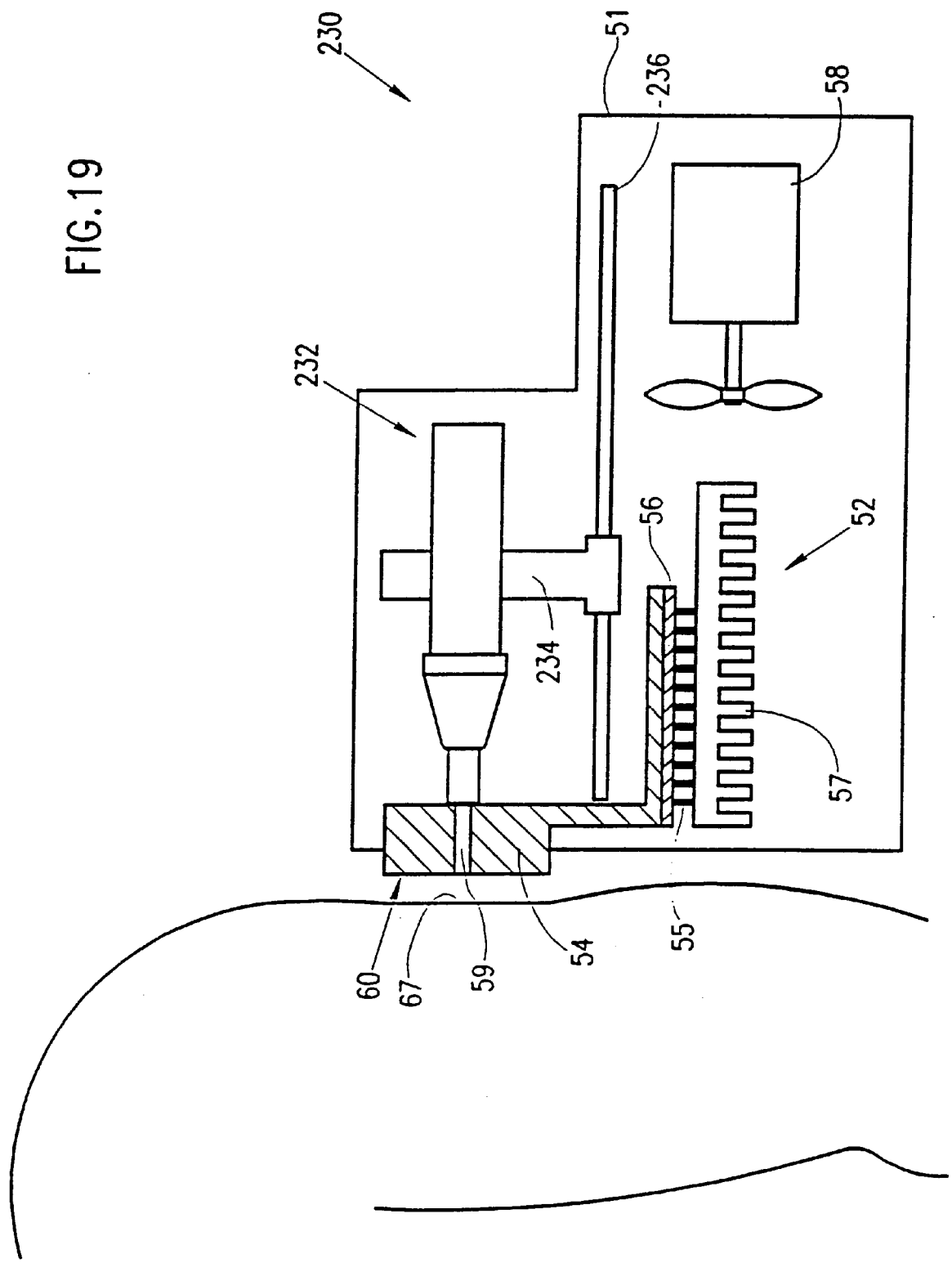
FIG. 19 is a schematic side view illustration of a manually operated jet injection device constructed and operative in accordance with an alternative embodiment of the invention.
Figure 20:
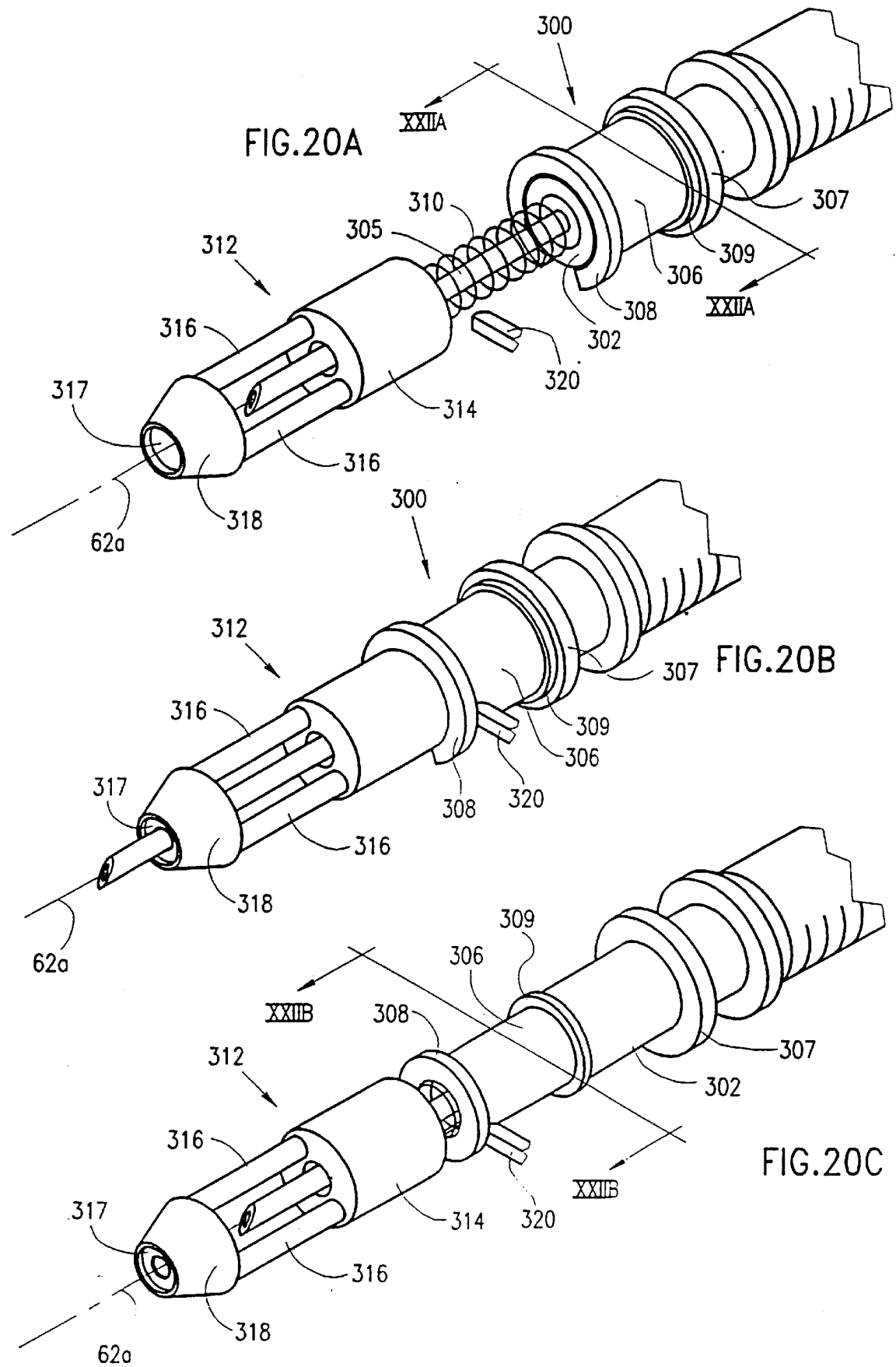
FIGS. 20A, 20B and 20C are pictorial illustrations of another preferred embodiment of the present invention in three different operative orientations.

Reference is now made to FIG. 19, in which is shown a jet injection device, referenced generally 230. Device 230 is typically similar to device 50 (FIG. 5A) except that injector assembly 53 thereof is replaced in the present embodiment by a jet injection assembly 232. Assembly 232 is supported in a stationary position in housing 51 via suitable support members 234 and 236. Assembly 232 may be any suitable jet injection apparatus, of which a suitable type is manufactured by Mada Equipment Company Inc. of 60 Commerce Road, Carlstadt, N.J. 07072, USA.

Reference is now made to FIGS. 20A–22B, which illustrate alternative embodiments of the present invention. FIGS. 20A–20C and FIGS. 22A and 22B illustrate a needle protector assembly 300 including an inner portion 302 having a recess 303 which is removably seated onto a needle mount protrusion 304 forming part of a conventional syringe. Inner portion 302 is arranged in coaxial frictional engagement with a needle 305 or may be glued or press fit thereto. Assembly 300 also includes an outer, axially slit, generally cylindrical gripping sleeve member 306, which is slidable with respect to inner portion 302.

The inner portion 302 of assembly 300 includes a rearward shoulder 307, while sleeve member 306 includes a forward shoulder portion 308 and a rearward shoulder portion 309.

Figure 21:
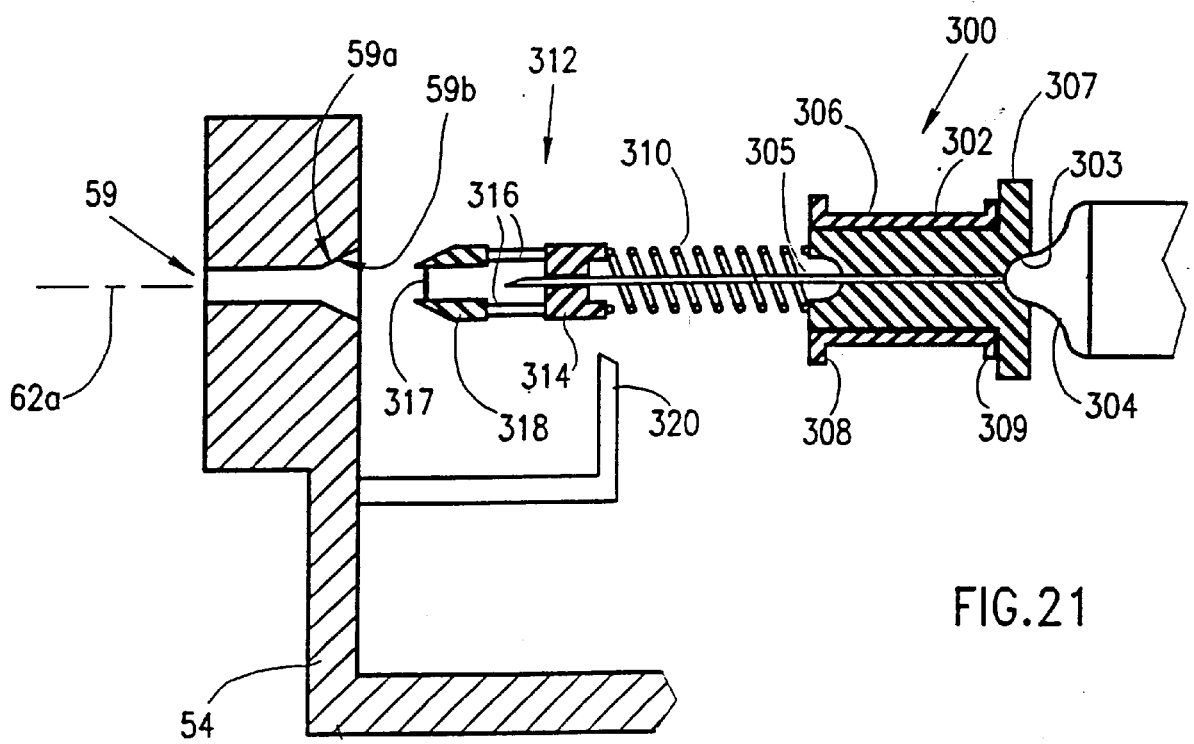
FIG. 21 is a sectional illustration of an embodiment of the invention incorporating the apparatus of FIGS. 20A, 20B and 20C.

Seated and retained on base assembly 300, in co-axial surrounding relationship with needle 305 is a spring 310. Seated and retained on an opposite end of spring 310 from base assembly 300 is a guide assembly 312. Guide assembly 312 includes a rearward guide member 314 which is attached by a plurality of shafts 316 to a forward guide member 318. Forward guide member 318 is arranged to seat in a tapered recess portion of aperture 59 in cooling plate 54 (FIG. 21).

An easily pierced cap member 317 may be located at the forward end of guide member 318 for wiping the needle 305 as it passes thereby preventing liquid contact between the needle 305 and the cooling plate 54, thus preserving sterility of the needle even when the cooling plate is not sterile.

Figure 22A:
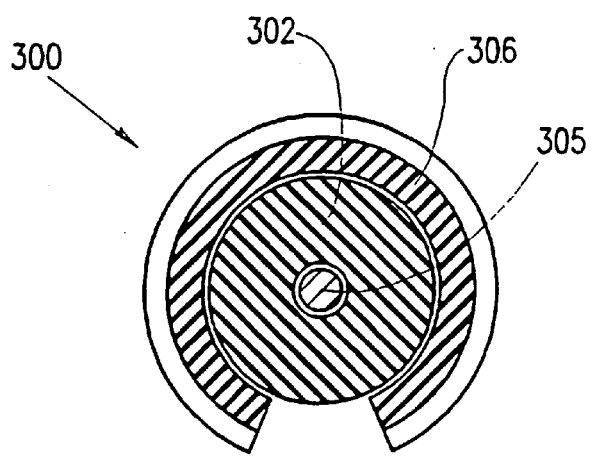
FIGS. 22A and 22B are sectional illustrations taken at lines XXIIA and XXIIB respectively in FIGS. 20A and 20B respectively.
Figure 22B:
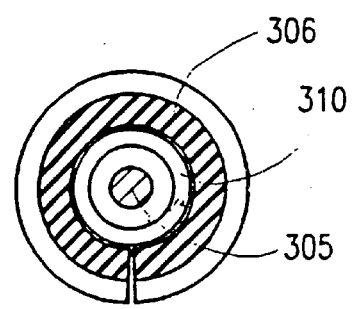

The operation of the apparatus of FIGS. 21–22B will now be described with reference to FIGS. 20A–20C. Prior to injection, the orientation of the apparatus is as shown in FIG. 20A and the inner and outer members 302 and 306 of the needle protector assembly 300 are in nested orientation. During injection, as seen in FIG. 20B, the entire syringe and the needle 305 are moved forward along axis 62a, as spring 310 is compressed, until shoulder 308 abuts the rearward end of rearward guide member 314. In this forward motion, shoulder 308 passes a ratchet finger 320 which is mounted onto cooled plate 54.

Following completion of the injection, the syringe and the needle are retracted along axis 62a, but shoulder 308 of the outer member 306 is retained against retraction by finger 320, as seen in FIG. 20C. As a result, inner member 302 slides rearwardly out from inside outer sleeve member 306, allowing member 306 to compress radially inwardly towards the needle 305, as can be appreciated by comparing FIGS. 22B and 22A.

This radially inward movement causes outer sleeve 306 to be incapable of axially sliding over inner member 302, such that outer sleeve 306 henceforth acts as a spacer between member 302 and rearward guiding member 314, thus preventing the pointed end of the needle 305 from again extending beyond the forward guide member 318.

It is a particular feature of the present invention that the pointed end of needle 305, when in a protected orientation, is nevertheless fully visible and accessible.

It will be appreciated by persons skilled in the art that the present invention is not limited to what has been shown and described hereinabove by way of example. The scope of the invention is limited, rather, solely by the claims which follow.

We claim:

1. Apparatus for piercing skin comprising:
   a skin contact surface arranged to be in thermal contact with a region of skin to be pierced;
   a jet injection device arranged to pierce said skin within said region; and
   a cooling assembly providing cooling of said skin contact surface thereby cooling said portion of skin prior to and during piercing thereof by said jet injection device.

2. Apparatus according to claim 1, and wherein said cooling assembly comprises a thermoelectric cooling assembly.

3. Apparatus according to claim 1, and wherein said jet injection device pricks said skin to allow withdrawal of fluids therefrom.

4. Apparatus according to claim 2, and wherein said jet injection device pricks said skin to allow withdrawal of fluids therefrom.

5. Apparatus according to claim 1, and wherein said jet injection device injects a jet hypodermically.

6. Apparatus according to claim 2, and wherein said jet injection device injects a jet hypodermically.

7. Apparatus according to claim 1, and wherein said jet injection device injects a jet intramuscularly.

8. Apparatus according to claim 2, and wherein said jet injection device injects a jet intramuscularly.

9. Apparatus according to claim 1 and wherein said cooled surface is formed with an aperture for passing a jet therethrough.

10. Apparatus according to claim 2 and wherein said cooled surface is formed with an aperture for passing a jet therethrough.

* * * * *